US010597700B2

(12) United States Patent
Navarro Y Garcia et al.

(10) Patent No.: US 10,597,700 B2
(45) Date of Patent: Mar. 24, 2020

(54) HIGH-THROUGHPUT SCREENING METHOD FOR THE IDENTIFICATION OF BIOMARKERS, THERAPEUTIC TARGETS OR THERAPEUTIC AGENTS

(71) Applicant: COMMISSARIAT À L'ÉNERGIE ATOMIQUE ET AUX ÉNERGIES ALTERNATIVES, Paris (FR)

(72) Inventors: Fabrice Navarro Y Garcia, Fontaine (FR); Jonathan Bruniaux, Grenoble (FR); Xavier Gidrol, Antony (FR); Eric Sulpice, Biviers (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 661 days.

(21) Appl. No.: 14/648,526

(22) PCT Filed: Dec. 2, 2013

(86) PCT No.: PCT/EP2013/075279
§ 371 (c)(1),
(2) Date: May 29, 2015

(87) PCT Pub. No.: WO2014/083205
PCT Pub. Date: Jun. 5, 2014

(65) Prior Publication Data
US 2015/0322494 A1 Nov. 12, 2015

(30) Foreign Application Priority Data

Nov. 30, 2012 (FR) ...................................... 12 61520

(51) Int. Cl.
*C12Q 1/68* (2018.01)
*C12Q 1/6809* (2018.01)
(52) U.S. Cl.
CPC ................................. *C12Q 1/6809* (2013.01)
(58) Field of Classification Search
CPC ................................ C12Q 1/68; C12Q 1/6809
See application file for complete search history.

(56) References Cited

U.S. PATENT DOCUMENTS

| | | | | |
|---|---|---|---|---|
| 6,974,669 | B2 * | 12/2005 | Mirkin | C12Q 1/6834 435/5 |
| 9,080,186 | B2 * | 7/2015 | Cui | A61K 9/0014 |
| 2009/0221684 | A1 | 9/2009 | Grinstaff et al. | |
| 2011/0171749 | A1 * | 7/2011 | Alocilja | B82Y 5/00 436/501 |
| 2011/0201695 | A1 | 8/2011 | Mourier-Robert et al. | |
| 2012/0021044 | A1 * | 1/2012 | Oh | C07C 237/06 424/450 |
| 2012/0289584 | A1 | 11/2012 | Cui et al. | |
| 2012/0316074 | A1 * | 12/2012 | Saxonov | C12N 15/10 506/2 |
| 2014/0077732 | A1 | 3/2014 | Modolo | |
| 2014/0094383 | A1 * | 4/2014 | Lee | G01N 33/5432 506/9 |
| 2014/0212498 | A1 * | 7/2014 | Brito | A61K 39/155 424/489 |

FOREIGN PATENT DOCUMENTS

| | | | | |
|---|---|---|---|---|
| WO | WO-2006078289 | A2 * | 7/2006 | ........... C12Q 1/6816 |
| WO | WO-2010018222 | A1 * | 2/2010 | ........... A61K 9/0019 |
| WO | WO2010018223 | | 2/2010 | |
| WO | WO-2012/019765 | | 2/2012 | |

OTHER PUBLICATIONS

Agasti et al., Nanoparticles for Detection and Diagnosis, Advanced Drug Delivery Reviews, 2010, 62, 316-328. (Year: 2010).*
Kawadkar et al., Nanobiotechnology: Application of Nanotechnology in Diagnosis, Drug Discovery and Drug Development, Asian Journal of Pharmaceutical and Clinical Research, 2011, 4(1), 23-28. (Year: 2011).*
Teixeira, et al., "Submicron Cationic Emulsions as a New Delivery System for Oligonucleotides", 1999, pp. 30-36, vol. 16, No. 1, Pharmaceutical Research.
Verzijlbergen, "A Barcode Screen for Epigenetic Regulators Reveals Role for the NuB4/HAT-B Histone Acetyltransferase Complex in Histone Turnover", Oct. 2011, pp. 1-15, vol. 7, No. 10, PLoS Genetics.
International Search Report dated Dec. 16, 2013 in PCT/EP2013/075279.
Berns, et al. "A large-scale RNAi screen in human cells identifies new components of the p53 pathway", Nature: International Weekly Journal of Science (and Supplementary Information), Nature Publishing Group, United Kingdom, vol. 428, Mar. 25, 2004, pp. 431-437, XP003002475.
Yang, et al, "Systemic delivery of siRNA with cationic lipid assisted PEG-PLA nanoparticles for cancer therapy" Journal of Controlled Release, Elsevier, Amsterdam, NL, vol. 156, No. 2, Jul. 26, 2011, pp. 203-211, XP028112013.
Santel, et al., "A novel siRNA-lipoplex technology for RNA interference in the mouse vascular endothelium" Gene Therapy, Nature Publishing Group, GB, vol. 13, No. 16, Apr. 20, 2006, pp. 1222-1234, XP002459352.
Gerrits, et al., "Cellular barcoding tool for clonal analysis in the hematopoietic system", Apr. 1, 2010, pp. 2610-2618, vol. 115, No. 13, Blood.
Dalesandro, et al, "Gene Therapy for Donor Hearts: Ex Vivo Liposome-Mediated Transfection", Feb. 1996, pp. 416-422, vol. 111, No. 2, The Journal of Thoracic and Cardiovascular Surgery.
Chono, et al., An efficient and low immunostimulatory nanoparticle formulation for system siRNA delivery to the tumor, 2008, pp. 64-69, vol. 131, Journal of Controlled Release.

(Continued)

Primary Examiner — Amy M Bunker
(74) Attorney, Agent, or Firm — B. Aaron Schulman, Esq.; Stites & Harbison PLLC

(57) ABSTRACT

The present invention relates to a method for screening a molecule of interest by means of nanoparticles comprising a candidate molecule, a tracer, and a single DNA tag specific to said molecule. The present invention also relates to a method for screening biomarkers of a disease and/or of a phenotype feature, more particularly of a cancer or an infection, by means of said nanoparticles. The invention finally relates to the nanoparticles as such as well as to a library of said nanoparticles.

10 Claims, 11 Drawing Sheets

(56) References Cited

OTHER PUBLICATIONS

Cui, et al., "Topical immunization using nanoengineered genetic vaccines", 2002, pp. 173-184, vol. 81, Journal of Controlled Release.
Marler ,et al., "Transplantation of cells in matrices for tissue regeneration", 1998, pp. 165-182, vol. 33, Advanced Drug Delivery Reviews.

* cited by examiner

M: molecular weight marker
1: 11/20
2: 5.5/10
3: 2.75/5
4: 1.37/2.5
5: 0.68/1.25
6: 0.34/0.62
7: 0.17/0.31
} ng of siRNA / ng DNA tag used for complexing with the nanoparticles
8: siRNA (0.17 ng) without nanoparticles
9: DNA tag (0.31 ng) without nanoparticles

HIGH-THROUGHPUT SCREENING METHOD FOR THE IDENTIFICATION OF BIOMARKERS, THERAPEUTIC TARGETS OR THERAPEUTIC AGENTS

The present invention relates to a method for screening a molecule of interest by means of nanoparticles comprising a candidate molecule, a tracer, and a single DNA tag specific to said molecule. The present invention also relates to a method for screening biomarkers of a disease and/or of a phenotypic trait, more particularly of a cancer or of an infection, by means of said nanoparticles. The invention finally relates to nanoparticles as such as well as to a library of said nanoparticles.

Reverse genetic engineering tries to determine the function of a given gene by analysing the phenotypic consequences of the mutation of this gene. This approach «is opposed» (reverse) to the conventional approach which, for a given phenotype mutant, tries to identify the responsible gene. Reverse genetic screens have thus for example allowed identification of key regulators of the cell cycle in yeasts (Hartwell et al., 1974, Science, 183:46-51), or of the basic principles of the mechanisms for developing multicellular organisms in Drosophila (Nussleinvolhard et Wieschaus, 1980, Nature, 287:795-801).

Reverse genetic screens may be based on function gains (over expression of a gene by means of an expression vector, of a microRNA analog, etc . . . ) or on function losses caused by chemical inhibitors of proteins or interfering RNAs (iRNAs). Chemical screens (an approach sometimes designated as a chemogenome approach) have allowed, via inhibition of the proteins, the discovery of many molecules today tested in clinical trials, or even already present on the market as a drug.

RNA interference (iRNA) is a natural process, preserved during evolution, according to which the introduction of double-strand RNA into a cell causes specific degradation of mRNA homologous sequences (Fire et al., 1998, Nature 391:806-811). Also, microRNAs (miRNA) are small endogenic non-coding RNAs, present in the genome, which specifically regulate the expression of a few target genes. There exist many other small non-coding RNAs (piRNA, natsiRNA, etc . . . ) which are involved in the regulation of the expression of the genes.

In fine, it should be kept in mind that the specific inhibition of a protein by a chemical inhibitor, the «function loss» mutation of a gene or the suppression of the expression of a protein by endogenic iRNA (miRNA) or exogenous RNA (siRNA) are functionally equivalent.

iRNA therefore provides an extremely powerful reverse genetic method, especially for organisms where conventional genetics is difficult like in humans. From sequences of the human genome, iRNA collections targeting the totality of the genes were developed, allowing reverse genetic screens to be made on human cell lines, or even on human primary cells (Boutros and Ahringer, 2008, Nature Reviews Genetics 9:554-566). Several recent studies have shown the power of large scale iRNA screens for characterizing the clinical relevance of particular genes for the individual response of patients to treatment. Further, with the recent development of miRNA inhibitors such as «locked nucleic acid (LNA)» modified oligonucleotides (Orom et al., 2006, Gene, 372: 137-141), anti-miRNA oligonucleotides (AMOs) (Weiler et al., 2006, Gene Therapy, 13: 496-502) and «antagomirs» (Krutzfeldt et al., 2005, Nature, 438: 685-689), genetic screens based on function loss of miRNAs are also possible. Moreover, the development of analogs of miRNA, of piRNA, etc . . . also allows functional high throughput screens with a function gain with these molecules.

To this day, the very large majority of high throughput cell screens use microtitration plates or chips with 96 or 384 wells which are read out (captured) with an automated microscope or a spectrophotometric (UV, visible, IR) reader of plates.

However, this plate or chip approach suffers from many limitations. Firstly, plates like chips require preliminary ordering of the candidate molecules (collections of chemical agents or nucleic acids) which will be used during the screening and tracking of this ordering in order to again find the molecules at the origin of the studied phenotype. Secondly, it is difficult to carry out these screenings on suspended cells (like blood cells), 3D culture cells, mixed cell populations, co-cultivated cells or cells requiring a nutrient layer (feeder layer). Thirdly, the tracking of the cells having incorporated the candidate molecule is difficult because it requires preliminary marking of each of these chemical or genetic molecules, this marking may alter their efficiency. Fourthly, these formats require complex image analysis methods both at the algorithmic level, and for storing and saving data. Fifthly, the recovery of the cells after analysis is very difficult, or even impossible. Sixthly, and as a corollary of the preceding limitation, the culture surface area available in the plates or the chips limits the studied phenotypes (not more than 72 h). The analysis of phenotypes requiring more time, such as for example the differentiation in a particular line, is impossible without recovering the cells and transferring them into another culture format.

In order to reply to a few of these limitations, the use of a nucleic bar code system borne by viral vectors was proposed for identifying downstream, with dedicated DNA chips, the nucleic acids responsible for the studied phenotype (Berns et al., 2004, Nature, 428:431-7). Several developments of this concept have been proposed since that time (Verzijlbergen et al., 2011, PLoS Genet, 10:e1002284). However, this approach itself has also several limitations. Firstly, it cannot be contemplated for chemical molecules. Secondly, developed for interfering RNAs transcribed and processed by cell machinery, it does not operate with other types of nucleic acids, non-processed by the cell like LNAs or analogs of miRNA, of piRNA, etc. Thirdly, it is based on the use of viruses and therefore requires laboratory manipulations at least of the L2 type and ideally of the L3 type. Fourthly, the use of a sequence modified by a bar code (i.e. a DNA tag) risks interceding in the interfering RNA process and it is not sure that the processing of iRNA and the extinction efficiency be systematically preserved with these viral constructs. Fifthly, the viral infection may itself induce phenotype modifications independent of the candidate molecule.

The development of screening methods with which these limitations may be overcome, is therefore necessary.

The inventors thus developed an approach without preliminary ordering of the candidate molecules, associated with phenotype readout at the individual cell level and with very high throughout sorting of the cells of interest, based on the use of nanoparticles giving the possibility of simultaneously «delivering», within a cell, a candidate molecule, a tracer allowing specific tracking of the molecules having incorporated the candidate molecule, and a single DNA tag specific to the candidate molecule allowing identification of the candidate molecule a posteriori, after readout of the phenotype, by deconvolution of the single DNA tag. The simultaneous «delivery» capacity of the candidate molecule, of the tracer and of the DNA tag by the nanoparticle is notably due to the size (less than 1 micron, preferably less than 200 nm) and to the charge (preferably positive charge) of the nanoparticle which imparts to the latter significant penetration efficiency into the cells.

For this purpose, according to a first object, the present invention provides a method for screening a molecule of interest comprising the following steps:

a) putting cells into contact with a library of nanoparticles, each nanoparticle comprising a candidate molecule, a tracer and a single DNA tag specific to said candidate molecule, under conditions allowing said cells to be integrated into at least one of said nanoparticles, b) selecting the cells having integrated the tracer and having a phenotype of interest, c) identifying as a molecule of interest, the candidate molecule having been integrated into the cell selected in step b) by identifying the sequence of said single DNA tag.

The present invention also relates to a method for screening a biomarker of a disease or of a phenotypic trait comprising the following steps:

a) putting cells in contact with a library of nanoparticles, each nanoparticle comprising a candidate molecule, a tracer and a single DNA tag specific to said candidate molecule, under conditions allowing said cells to integrate at least one of said nanoparticles, b) selecting the cells having integrated the tracer and having a phenotype of interest, c) identifying the candidate molecule having been integrated into the cell selected in step b) by identifying the sequence of said single DNA tag, d) identifying as a biomarker of a disease and/or of a phenotype feature the target of said molecule identified in step c).

Optionally, said methods for screening a molecule of interest or a biomarker of a disease or of a phenotype feature comprised, before step a), a step a0) for preparing a library of nanoparticles, each nanoparticle comprising a candidate molecule, a tracer and a single DNA tag specific to said candidate molecule.

The invention also relates to the use of a nanoparticle comprising a candidate molecule, a tracer and a single DNA tag specific to said candidate molecule for screening molecules of interest and/or of a biomarker of a disease and/or of a phenotype.

According to another object, the invention relates to a nanoparticle comprising a candidate molecule, a tracer and a single DNA tag specific to said candidate molecule.

The invention also relates to a library of nanoparticles, each of said nanoparticles comprising a candidate molecule, a tracer and a single DNA tag specific to said candidate molecule.

A NANOPARTICLE COMPRISING A CANDIDATE MOLECULE, A TRACER AND A SINGLE DNA TAG SPECIFIC TO SAID CANDIDATE MOLECULE

The invention relates to a nanoparticle comprising a candidate molecule, a tracer and a single DNA tag specific to said candidate molecule.

The nanoparticle may be a neutral, anionic or cationic nanoparticle. Preferably, said nanoparticle is a cationic nanoparticle. The nanoparticle is notably a synthetic nanoparticle. The use of a synthetic nanoparticle gives the possibility of carrying out not very restrictive manipulations, as compared with manipulations applying microorganisms or viruses. In certain embodiments, said nanoparticle is an inorganic nanoparticle, such as for example a gold nanoparticle, a magnetic nanoparticle (iron oxide nanoparticle), or a nanocrystal of a semi-conducting material ("quantum dot"). In certain embodiments, said nanoparticle is an organic nanoparticle such as for example a cationic vector. Examples of nanoparticles which may be used in the invention are notably described in Morille et al., 2008, Biomaterials, 29:3477-3496; Bruno, 2011, Advanced Drug Delivery Reviews, 63:1210-1226 ; Zhang et al., 2012, Bioorganic Chemistry, 40:10-18. In certain embodiments, said nanoparticle is a hybrid nanoparticle, i.e. a nanoparticle including an inorganic core covered with a polymeric layer.

In an embodiment, said cationic vector is formulated from at least one polymer. Examples of polymers are polyethyleneimine (PEI), poly(L-lysine) (PLL), poly($\alpha$-[4-aminobutyl]-L-glycolic acid), chitosan, such as galactosylated chitosan, galactosylated chitosan-graft-poly(vinylpyrrolidone) (PVP), trimethylated chitosan oligomers, N-dodecyl chitosan, modified chitosan deoxycholic acid, polyamidoamine (PAMAM), poly(lactic acid) (PLA), poly(lactic-co-glycolic acid) (PLGA), polyalkylcyanoacrylate (PACA), cyanoacrylate derivatives, such as polybutylcyanoacrylate (PBCA), polyisobutylcyanoacrylate (PIBCA), polyisohexylcyanoacrylate (PIHCA), polyhexylcyanoacrylate (PHCA), or isobutylcyanoacrylate (IBCA). Optionally, said vector may further comprise at least one polyethylene-glycol (PEG).

In an embodiment, said cationic vector is a cationic lipid vector, i.e. a cationic or polycationic derivative of a lipid nature capable of interacting via an electrostatic effect with a negatively charged candidate molecule. Preferably, said cationic lipid vector is a liposome, or a droplet of a formulation in the form of a nanoemulsion comprising a continuous aqueous phase and at least one dispersed phase.

Preferably, said liposome comprises or consists in at least one monovalent aliphatic lipid, such as 1,2-dioleyl-3-trimethylamonium-propane (DOTAP), N[1-(2,3-dioleyloxy)propyl]-N,N,N-trimethylammonium (DOTMA), or N-(2-hydroxyethyl)-N,N-dimethyl-2,3-bis(tetradecyloxy-1-propananium) (DMRIE), a multivalent aliphatic lipoid, such as dioctadecylamidoglycylspermine (DOGS), or a cationic derivative of cholesterol, such as 3$\beta$-[N-(N',N'-dimethylamminoethane)-carbamoyl]cholesterol (DC-Chol) or bis-guanidium-tren-cholesterol (BGTC). Optionally, said liposome may further comprise a fusogenic lipid, which may facilitate cytosolic release by destabilization of the endosomal membrane, a so called "helper" lipid, such as diol-eylphosphatidylethanolamine (DOPE) or cholesterol. Said liposome may comprise at least 2, 3, 4, 5 lipids as described above. As non-limiting examples, said liposome may therefore be a DOTMA/DOPE or DOTAP/cholesterol liposome. Optionally, said vector may further comprise at least one poly-ethylene-glycol (PEG). Examples of liposomes further comprising at least one PEG are liposomes consisting of N,N-dioleyl-N,N-dimethylammonium chloride, of DOPE and of conjugate ceramides, of a PEG, liposomes consisting of 3-N-[methoxypoly(ethyleneglycol)$_{2000}$)carbamoyl]-1,2-dimyristoyloxy-propylamine (PEG-C-DMA), 1,2-dilinoleyloxy-N—N-dimethyl-3-aminopropane (DLinDMA), 1,2-distearoyl-sn-glycero-3-phosphocholine (DSPC) and cholesterol at a ratio of 2:40:10:48 in molar percent, of the liposomes consisting of $\beta$-L-arginyl-2,3-L-diaminopropionic acid-N-palmityl-N-oleyl-amide trihydrochloride, 1,2-diphytanoyl-sn-glycero-3-phosphoethanolamine (DphyPE and sodium PEGylated N-(carbonyl methoxypolyethyleneglycol-2000)-1,2-distearoyl-sn-glycero-3-phospho-ethanolamine (DSPE-PEG), liposomes consisting of soya hydrogenated phosphatidyl choline, DSPE-PEG2000 and DOTAP.

Preferably, said droplet of a formulation in the form of a nanoemulsion, comprising a continuous aqueous phase and at least one dispersed phase, is as defined in application FR 12 58115. According to this embodiment, said droplet of a formulation in the form of a nanoemulsion, comprising a continuous aqueous phase and at least one dispersed phase comprises:
a) at least 5% molar of amphiphilic lipid,
b) from 15 to 70% molar of at least one cationic surfactant comprising:
  i) at least one lipophilic group selected from:
    a group R or R-(C=O)-, wherein R represents a linear hydrocarbon chain comprising from 11 to 23 carbon atoms,
    an ester or an amide of fatty acids comprising from 12 to 24 carbon atoms and of phosphatidylethanolamine, and
    a poly(propylene oxide), and
  ii) at least one hydrophilic group comprising at least one cationic group selected from:
    a linear or branched alkyl group comprising from 1 to 12 carbon atoms and interrupted and/or substituted with at least one cationic group, and
    a hydrophilic polymeric group comprising at least one cationic group, and
c) from 10% to 55% molar of a co-surfactant comprising at least one poly(ethylene oxide) chain comprising at least 25 ethylene oxide units,
d) a solubilizing lipid comprising at least one fatty acid glyceride,
e) optionally a fusogenic lipid,
wherein the molar percentages of amphiphilic lipid, of cationic surfactant and of co-surfactant are relatively to the (amphiphilic lipid/cationic surfactant/co-surfactant/optional fusogenic lipid) assembly.

As explained hereafter, the substances: amphiphilic lipid/cationic surfactant/co-surfactant/optional fusogenic lipid are the main components of the crown of the droplets of the formulation.

The emulsion is therefore an emulsion of the oil-in-water type. It may be simple or multiple, notably by including in the dispersed phase, a second aqueous phase. Preferably, it is simple.

Further, the formulation is advantageously stable: it may be stored for several hours or weeks without observation of any degradation.

Said formulation is particularly suitable for being complexed to negatively charged molecules, such as for example nucleotide sequences which may modulate interfering RNA endogenous mechanisms.

Cationic Surfactant

The formulation used in the invention comprises a cationic surfactant comprising:
a) at least one lipophilic group selected from:
  i) a group R representing a linear hydrocarbon chain comprising from 11 to 23 carbon atoms,
  ii) an ester or an amide of fatty acids comprising from 12 to 24 carbon atoms and of phosphatidylethanolamine, such as distearyl phosphatidylethanolamine (DSPE), and
  iii) a poly(propylene oxide), and
b) at least one hydrophilic group comprising at least one cationic group selected from:

i) a linear or branched alkyl group comprising from 1 to 12 carbon atoms and interrupted and/or substituted with at least one cationic group, and
ii) a hydrophilic polymeric group comprising at least one cationic group, said polymeric group notably being selected from:
  a poly(ethylene oxide) typically comprising from 3 to 500 ethylene oxide units, preferably from 20 to 200 ethylene oxide units, and comprising at least one cationic group.
  a polysaccharide, such as dextran, cellulose or chitosan, notably having molecular masses comprised between 0.5 and 20 kDa, for example between 1 and 12 kDa,
  a polyamine, such as a chitosan or a polylysine, notably having molecular masses comprised between 0.5 and 20 kDa, for example between 1 and 12 kDa.

By «ester or amide of fatty acids comprising from 12 to 24 carbon atoms and phosphatidylethanolamine», is meant a group of formula:

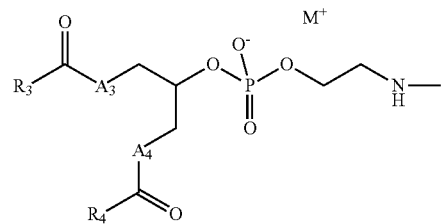

wherein
$R_3$ and $R_4$ independently represent a linear hydrocarbon chain comprising from 11 to 23 carbon atoms,
$A_3$ and $A_4$ represent O or NH, and
M represents H or a cation.

The cationic groups of the cationic surfactant are typically:
  oniums selected from ammonium, imidazolium, pyridinium, pyrrolidinium, piperidinium, phosphonium or sulfonium groups, or
  metal complexes between a radical of a mono- or multidentate chelating organic group, for example phenantroline, pyridine, ethylene diamine tetraacetic acid (EDTA), diethylene triamine penta acetic acid (DTPA), porphyrins, phtalocyanins, chlorines, bacteriochlorines complexed with an inorganic cation, such as $Ca^{2+}$, $Al^{3+}$, $Ni^+$, $Zn^{2+}$, $Fe^{2+}$, $Fe^{3+}$ or $Cu^{2+}$, ammonium groups, notably $—^+NMe_3$, $—^+NHMe_2$, $—^+NH_2Me$ and $—^+NH_3$, in particular $—^+NH_3$, being particularly preferred.

Of course, anions may be associated with the cationic group(s) so that the formulation is electrically neutral. The nature of the anions is not limited, as an illustration, mention may be made of halides, notably chloride or bromide, or trifluoroacetate.

In the cationic surfactant, the nature of the bond group binding the lipophilic group(s) to the hydrophilic group(s) comprising at least one cationic group is not limited. Examples of bond groups are provided below (group L).

In an embodiment, the cationic surfactant has the following formula (A):

$$[(Lipo)_l\text{-}L\text{-}(Hydro)_h]^{n+}, (n/m)[A]^{m-} \qquad (A)$$

wherein:
l and h represent integers independently comprised between 1 and 4,
n is an integer greater than or equal to 1, generally comprised between 1 and 50,
Lipo represents a lipophilic group as defined above,
Hydro represents a hydrophilic group as defined above comprising at least one cationic group,
L represents a bond group,
A represents an anion,
m is an integer representing the charge of the anion,
n is an integer representing the charge of the cation $[(Lipo)_l\text{-}L\text{-}(Hydro)_h]$.

In the aforementioned formula (A), preferably L is such that:
a) when l and h represent 1, L is a divalent binding group selected from:
a simple bond,
a group Z selected from —O—, —NH—, —O(OC)—, —(CO)O—, —(CO)NH—, —NH(CO)—, —O—(CO)—O—, —NH—(CO)—O—, —O—(CO)—NH— and —NH—(CO)—NH, —O—PO(OH)—O—
or a cyclic divalent radical of 5 to 6 atoms,
an Alk group being an alkylene comprising from 1 to 6 carbon atoms, and
a Z-Alk, Alk-Z, Alk-Z-Alk or Z-Alk-Z group wherein Alk and Z are as defined above and wherein both groups Z of the group Z-Alk-Z are identical or different,
b) when one of the groups l or h represent 1, and the other one represents 2, L is a trivalent group selected from a phosphate group OP—(O—)$_3$, a group derived from glycerol of formula —O—CH$_2$—CH—(O—)CH$_2$—O— and a cyclic trivalent radical of 5 to 6 atoms,
for the other values of l and h, L is a cyclic multivalent radical of 5 to 6 atoms.
More preferably, L is such that:
a) when l and h represent 1, L is a divalent binding group selected from:
a simple bond,
a Z group selected from —O—, —NH—, —O—(OC)—, —(CO)O—, —(CO)NH—, —NH(CO)—, —O—(CO)—O—, —NH—(CO)—, —O—(CO)—NH— and —NH—(CO)—NH or —O—PO(OH)—O—,
b) when one of the groups l or h represents 1, and the other one represents 2, L is a trivalent group selected from a phosphate group OP—(O—)$_3$ and a group derived from glycerol of formula —O—CH$_2$—CH—(O—)CH$_2$—O—.

In the aforementioned formula (A), l and h preferably represent independently 1 or 2.

According to a first alternative, the hydrophilic group of the cationic surfactant is a linear or branched alkyl group comprising from 1 to 12 carbon atoms and interrupted and/or substituted with at least one cationic group. As an example of such cationic surfactants, mention may be made of:
1) (Lipo)-(CH$_2$)$_{m1}$—NR$_{30}$R$_{31}$R$_{32}$, wherein Lipo is a lipophilic group as defined above, m1 represents 1 or 2 and R$_{30}$, R$_{31}$ and R$_{32}$ represent independently H, Me or —CH$_2$—CH$_2$—OH,
2)

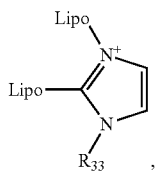

wherein each Lipo is independently a lipophilic group as defined above, and R$_{33}$ represents H, Me or —CH$_2$—CH$_2$—OH,
3)

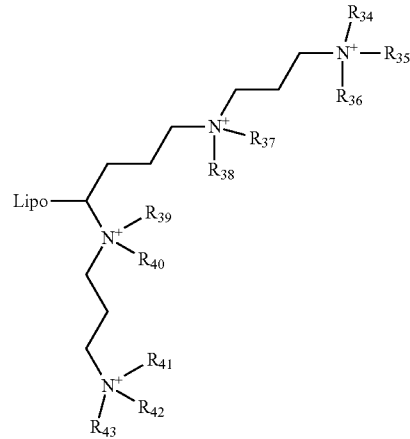

wherein Lipo is a lipophilic group as defined above, and R$_{34}$, R$_{35}$, R$_{36}$, R$_{37}$, R$_{38}$, R$_{39}$, R$_{40}$, R$_{41}$, R$_{42}$ and R$_{43}$ represent independently H, Me or —CH$_2$—CH$_2$—OH.

In an embodiment, the cationic surfactant is selected from:
N[1-(2,3-dioleyloxy) propyl]-N,N,N-trimethylammonium (DOTMA),
1,2-dioleyl-3-trimethylamonium-propane (DOTAP),
N-(2-hydroxyethyl)-N,N-dimethyl-2,3-bis(tetradecyloxy-1-propananium) (DMRIE),
1-[2-(oleoyloxy)ethyl]-2-oleyl-3-(2-hydroxyethyl)imidazolinium (DOTIM), and
dioctadecylamidoglycylspermine (DOGS) (in a protonated form), and is preferably 1,2-dioleyl-3-trimethylamonium-propane (DOTAP).

According to a second alternative, the hydrophilic group of the cationic surfactant is a hydrophilic polymeric group comprising at least one cationic group.

When the hydrophilic group of the cationic surfactant is polymeric, the cationic group(s) may be one of the terminal or pendant group(s). For example:
when the hydrophilic polymeric group is a poly(ethylene oxide), the cationic group(s) is (are) generally located on a terminal group at the end of the poly(ethylene oxide) chain.
when the hydrophilic polymeric group is dextran or cellulose, the cationic group(s) is (are) generally located on a terminal group at the end of the polysaccharide chain.
when the hydrophilic polymeric group is chitosan, the cationic group(s) is (are) generally one of the pendant group(s), in particular —NH$_3^+$ groups present in an acid medium on chitosan.

In an embodiment, the cationic group(s) is (are) one or more terminal group(s). Indeed, the pendant groups of anionic surfactants adjacent at the surface of the droplets of the dispersed phase are repelled by electrostatic interactions and, therefore, the formulations comprising cationic surfactants for which the Hydro group comprises pendant groups are generally less stable.

In another embodiment, the cationic group(s) is (are) one or more pendant groups. It is advantageously possible to use a cationic surfactant for which the hydrophilic group comprises several pendant cationic groups, and therefore obtain a more positively charged formulation, and which will allow much better the complexation of negative species such as for example the nucleotide sequences which may modulate interfering RNA endogenous mechanisms.

The preferred hydrophilic polymeric group is a radical of a poly(ethylene oxide) typically comprising from 3 to 500 ethylene oxide units, preferably from 20 to 200 ethylene oxide units, and comprising at least one cationic group.

Thus, in an embodiment, the cationic surfactant has one of the following formulae:

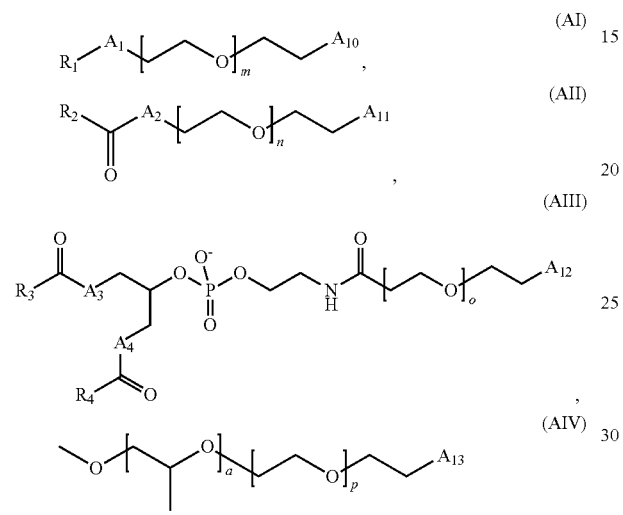

wherein:
$R_1$, $R_2$, $R_3$ and $R_4$ represent independently a linear hydrocarbon chain comprising from 11 to 23 carbon atoms,
$A_1$, $A_2$, $A_3$ and $A_4$ represent O or NH,
m, n, o and p represent independently integers from 3 to 500, preferably 20 to 200, and
a represents an integer from 20 to 120,
M represents H or a cation,
$A_{10}$, $A_{11}$, $A_{12}$ and $A_{13}$ represent independently a group $-^+NR_{20}R_{21}R_{22}$, wherein $R_{20}$, $R_{21}$ and $R_{22}$ represent independently H, Me or $-CH_2-CH_2-OH$.

In an embodiment, in formula (AII), $A_{11}$ represents $-^+NH_3$ and the cationic surfactant has the following formula:

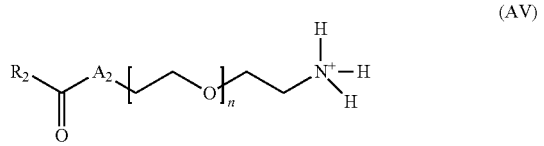

wherein $A_2$, $R_2$ and n are as defined above. Preferably, in formula (AII), $R_2$ represents $C_{17}H_{35}$.

Without intending to be bound to a particular theory, the presence of the hydrophilic polymeric group would allow:
stabilization of the formulation, and
protection of the molecules localised at the surface of the droplets, more particularly the nucleotide sequences which may modulate interfering RNA endogenous mechanisms, of the proteins of the medium into which the formulation is administered/used, and therefore the degradation of these molecules, more particularly of the nucleotide sequences which may modulate interfering RNA endogenous mechanisms, with these proteins.

According to a third alternative, the formulation according to the invention comprises at least two cationic surfactants, whereof:
a) one is selected from:
   N[1-(2,3-dioleyloxy) propyl]-N,N,N-trimethylammonium (DOTMA),
   1,2-dioleyl-3-trimethylamonium-propane (DOTAP),
   N-(2-hydroxyethyl)-N,N-dimethyl-2,3-bis(tetradecyloxy-1-propananium) (DMRIE),
   1-[2-(oleoyloxy)ethyl]-2-oleyl-3-(2-hydroxyethy)imidazolinium chloride (DOTIM), and
   dioctadecylamidoglycylspermine (DOGS), and is preferably 1,2-dioleyl-3-trimethylamonium-propane (DOTAP), and
b) the other one is a cationic surfactant comprising:
   i) at least one lipophilic group selected from:
      a group R or R—(C=O)—, wherein R represents a linear hydrocarbon chain comprising from 11 to 23 carbon atoms,
      an ester or an amide of fatty acid comprising from 12 to 24 carbon atoms and of phosphatidylethanolamine, such as distearyl phosphatidylethanolamine (DSPE), and
      a poly(propylene oxide), and
   ii) a hydrophilic polymeric group comprising at least one cationic group, said polymeric group being selected from:
      a poly(ethylene oxide) typically comprising from 3 to 500 ethylene oxide units, preferably from 20 to 200 ethylene oxide units, and comprising at least one cationic group,
      a polysaccharide, such as dextran, cellulose or chitosan,
      a polyamine, such as a chitosan or a polylysine, and is preferably a poly(ethylene oxide) comprising at least one cationic group.

In an embodiment, the formulation according to the invention comprises as cationic surfactants:
a) 1,2-dioleyl-3-trimethylamonium-propane, and
b) a cationic surfactant comprising:
   i) at least one lipophilic group selected from:
      a group R or R—(C=O)—, wherein R represents a linear hydrocarbon chain comprising from 11 to 23 carbon atoms,
      an ester or an amide of fatty acids comprising from 12 to 24 carbon atoms and of phosphatidylethanolamine, such as distearyl phosphatidylethanolamine (DSPE), and
   ii) a poly(ethylene oxide) typically comprising from 3 to 500 ethylene oxide units, preferably from 20 to 200 ethylene oxide units, and comprising at least one cationic group.

In an embodiment, the formulation according to the invention comprises, as cationic surfactants:
1,2-dioleyl-3-trimethylamonium-propane, and
a compound of formula (AII) as defined above, notably of formula (AV).

The cationic surfactant is located in the crown of the droplets of the formulation. It is bound by electrostatic interactions to negatively charged molecules, such as for example the nucleotide sequences which may modulate interfering RNA endogenous mechanisms and gives the possibility of maintaining these molecules at the surface of the droplets.

The formulation comprises from 15 to 70% molar of at least one cationic surfactant relatively to the (amphiphilic lipid/cationic surfactant/co-surfactant/optional fusogenic lipid) assembly. Below 15%, the formulation does not comprise enough of positive charges and the complexation of the formulation with negatively charged molecules (for example the nucleotide sequences which may modulate interfering RNA endogenous mechanisms) is insufficient. Beyond 70%, the formulations are not stable, and generally they cannot even be formulated (the formation of the nanoemulsion is not possible since the droplets coalesce in order to form two phases), and the droplets generally become toxic for cells.

These proportions are particularly suitable for obtaining efficient complexation of the negatively charged candidate molecules, such as the nucleotide sequences which may modulate interfering RNA endogenous mechanisms and therefore good delivery and/or transfection.

Fusogenic Lipid ("Helper Lipid")

In an embodiment, the formulation according to the invention comprises a fusogenic lipid, which may facilitate the cytosolic release by destabilization of the endosomal membrane, a so called "helper" lipid. Preferably, this lipid is dioleylphosphatidylethanolamine (DOPE).

This lipid gives the possibility of promoting endosomal escape of the droplets of the formulation according to the invention, and therefore of the candidate molecules, such as for example the nucleotide sequences which may modulate endogenous interfering mechanisms by RNA, which they contain, and generally improves the efficiency of said candidate molecules. For example, when the candidate molecule is a nucleotide sequence which may modulate endogenous interfering mechanisms by RNA, this lipid improves the genic extinction efficiency of said nucleotide sequence.

The lipid which may facilitate cystosolic release by destabilization of the endosomal membrane is located in the crown of the droplets of the formulation.

Amphiphilic Lipid

The formulation comprises at least one amphiphilic lipid, which is located in the crown of the droplets of the formulation.

In order to form a stable nanoemulsion, it is necessary to include into the composition at least one amphiphilic lipid as a surfactant. The amphiphilicity of the surfactant ensures stabilization of the oil droplets within the continuous aqueous phase. Below 5% molar of amphiphilic lipid relatively to the (amphiphilic lipid/cationic surfactant/co-surfactant/ optional fusogenic lipid) assembly, the formulations are not stable, and cannot generally even be formulated (the formation of the nanoemulsion is not possible since the droplets coalesce in order to form two phases).

Generally, the formulation comprises from 5 to 85% molar, preferably from 5 to 75% molar, in particular from 5 to 50% molar and most particularly from 8 to 30% molar of amphiphilic lipid relatively to the (amphiphilic lipid/cationic surfactant/co-surfactant/optional fusogenic lipid) assembly.

The amount of amphiphilic liquid advantageously contributes to controlling the size of the diverse phase of the nanoemulsion.

Amphiphilic lipids include a hydrophilic portion and a lipophilic portion. They are generally selected from compounds for which the lipophilic portion comprises a linear or branched, saturated or unsaturated chain having from 8 to 30 carbon atoms. They may be selected from phospholipids, cholesterols, lysolipids, sphingomyelins, tocopherols, glucolipids, stearylamines, cardiolipins of natural or synthetic origin; molecules consisting of a fatty acid coupled with a hydrophilic group through an ether or ester function such as sorbitan esters like for example sorbitan monooleate and monolaurate sold under the names of Span® by Sigma; polymerised lipids; conjugate lipids to short chains of polyethylene oxide (PEG) such as the non-ionic surfactants sold under the commercial names Tween® by ICI Americas, Inc. and Triton® by Union Carbide Corp.; sugar esters such as saccharose mono- and di-laurate, mono- and di-palmitate, mono- and di-stearate; said surfactants may be used alone or as mixtures.

Phospholipids are the preferred amphiphilic lipids.

Lecithin is the particularly preferred amphiphilic lipid.

Solubilizing Lipid

The formulation moreover comprises a solubilizing lipid comprising at least one fatty acid glyceride, which is located in the dispersed phase of the nanoemulsion, more specifically in the core of the droplets. This compound has the main mission of solubilizing the not very soluble amphiphilic lipid, in the dispersed phase of the nanoemulsion.

The solubilizing lipid is a lipid having sufficient affinity with the amphiphilic lipid so as to allow its solubilization. Preferably, the solubilizing lipid is solid at room temperature.

In the case when the amphiphilic lipid is a phospholipid, this may notably be:

esters of fatty acids and of fatty alcohol, such as cetyl palmitate, or derivatives of glycerol, in particular glycerides obtained by esterification of glycerol with fatty acids.

The solubilizing lipid used is advantageously selected depending on the amphiphilic lipid used. It will generally have a close chemical structure, in order to ensure the sought solubilization. This may be an oil or a wax. Preferably, the solubilizing lipid is solid at room temperature (20° C.), but liquid at body temperature (37° C.).

The preferred solubilizing lipids, in particular for phospholipids, are esters of fatty acids and of fatty alcohol, like cetyl palmitate, or glycerides of fatty acids, notably of saturated fatty acids, and in particular of saturated fatty acids including 8 to 18 carbon atoms, still preferably 12 to 18 carbon atoms. Advantageously, this is a mixture of different glycerides.

Preferably, these are glycerides of saturated fatty acids including at least 10% by weight of C12 fatty acids, at least 5% by weight of C14 fatty acids, at least 5% by weight of C16 fatty acids and at least 5% by weight of C18 fatty acids.

Preferably, these are glycerides of saturated fatty acids including 0% to 20% by weight of C8 fatty acids, 0% to 20% by weight of C10 fatty acids, 10% to 70% by weight of C12 fatty acids, 5% to 30% by weight of C14 fatty acids, 5% to 30% by weight of C16 fatty acids and 5% to 30% by weight of C18 fatty acids.

Mixtures of semi-synthetic glycerides solid at room temperature are particularly preferred, sold under the commercial name of Suppocire®NC by Gattefossé and approved for injection in humans. The Suppocire® of type N are obtained by direct esterification of fatty acids and of glycerol. These are hemi-synthetic glycerides of C8-C18 saturated fatty acids, for which the qualitative-quantitative composition is indicated in the table below.

The aforementioned solubilizing lipids give the possibility of obtaining a formulation in the form of an advantageously stable nanoemulsion. Without intended to be bound to a particular theory, it is assumed that the aforementioned solubilizing lipids give the possibility of obtaining droplets in the nanoemulsion having an amorphous core. The thereby obtained core has a high internal viscosity without, however, having crystallinity. Now, crystallisation is detrimental for the stability of the nanoemulsion since it generally leads to aggregation of the droplets and/or to expulsion of the molecules encapsulated on the outside of the droplets. These physical properties promote physical stability of the nanoemulsion.

The amount of solubilizing lipid may widely vary depending on the nature and on the amount of amphiphilic lipid present in the dispersed phase. Generally, the core of the droplets (comprising the solubilizing lipid, the optional oil, the optional imaging agent, the optional therapeutic agent if it is lipophilic) comprises from 1 to 100% by weight, preferably from 5 to 80% by weight and most particularly from 40 to 75% by weight of solubilizing lipid.

| Fatty acid composition of Suppocire ® NC from Gattefosse | |
|---|---|
| Chain length | [% by weight] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

Oil

The dispersed phase may moreover include one or several other oils, which are located in the core of the droplets.

The oils used preferably have a hydrophilic-lipophilic balance (HLB) of less than 8 and even more preferentially comprised between 3 and 6. Advantageously, the oils are used without any chemical or physical modification prior to the formation of the emulsion.

The oils are generally selected from biocompatible oils, and in particular from oils of natural origin (plant or animal oil) or of synthetic origin. Among such oils, mention may notably be made of oils of natural plant origin among which notably appear soybean, flax, palm, groundnut, olive, grape pip and sunflower oils; synthetic oils among which notably appear triglycerides, diglycerides and monoglycerides. These oils may be first pressed, refined or inter-esterified oils.

The preferred oils are soya oil and flax oil.

Generally, if present, the oil will be contained in the core of the droplets (comprising the solubilizing lipid, the optional oil, the optional imaging agent, the optional therapeutic agent if it is lipophilic) in a proportion ranging from 1 to 80% by weight, preferably between 5 and 50% by weight and most particularly 10 to 30% by weight.

The dispersed phase may further contain other additives such as colouring agents, stabilizers, preservatives, or other active ingredients, in a suitable amount.

Co-Surfactant

The formulation comprises a co-surfactant which allows stabilization of the nanoemulsion.

The co-surfactants which may be used in the formulations used in the invention are generally water-soluble surfactants. They comprise at least one poly(ethylene oxide) chain comprising at least 25, notably at least 30, preferably at least 35 ethylene oxide units. The number of ethylene oxide units is generally less than 500.

Formulations comprising a co-surfactant comprising a poly(ethylene oxide) chain comprising less than 25 ethylene oxide units are actually not stable. Generally, it is not even possible to prepare the nanoemulsion.

These numbers of units are actually particularly suitable for avoiding escape of the nucleotide sequences which may modulate interfering RNA endogenous mechanisms out of the droplets.

Indeed, the inventors observed that a formulation not comprising a co-surfactant is not sufficiently stable.

Further, without intending to be bound to a particular theory, the presence of the chain consisting of ethylene oxide units of the co-surfactant would allow protection of the negatively charged candidate molecules, and more particularly of the nucleotide sequences which may modulate interfering RNA endogenous mechanisms located at the surface of the droplets of the proteins of the medium in which the formulation is administered/used, and therefore the degradation of said negatively charged candidate molecules by these proteins.

As an example of co-surfactants, mention may in particular be made of conjugate polyethyleneglycol/phosphatidylethanolamine (PEG-PE) compounds, fatty acid and polyethyleneglycol ethers such as the products sold under the commercial names of Brij® (for example Brij® 35, 58, 78 or 98) by ICI Americas Inc., fatty acid and polyethyleneglycol esters such as the products sold under the commercial names of Myrj® by ICI Americas Inc. (for example Myrj® 45, 52, 53 or 59) and the block copolymers of ethylene oxide and propylene oxide such as the products sold under the commercial names of Pluronic® by BASF AG (for example Pluronic® F68, F127, L64, L61, 10R4, 17R2, 17R4, 25R2 or 25R4) or the products sold under the commercial name of Synperonic® by Unichema Chemie BV (for example Synperonic® PE/F68, PE/L61 or PE/L64).

Thus, the co-surfactant is located both in the continuous aqueous phase and in the dispersed phase. Indeed, the hydrophobic portion of the co-surfactant is inserted into the droplets of the dispersed phase, while the polyalkoxylated chains are in the continuous aqueous phase. In the present application, the mass percentages of dispersed phase described are calculated by considering that the co-surfactant belongs to the dispersed phase.

The formulation comprises from 10% to 55% molar of co-surfactant relatively to the (amphiphilic lipid/cationic surfactant/co-surfactant/optional fusogenic lipid) assembly. Below 10%, the formulations are not stable, and cannot generally be even formulated (the formation of the nanoemulsion is not possible since the droplets coalesce in order to form two phases). Beyond 55%, the complexation of the "premixed" formulation with the negatively charged candidate molecules, such as for example the nucleotide sequences, or with the DNA tags does not occur, probably since the positive charges of the cationic surfactant are masked by poly(ethylene oxide) chains of the co-surfactant, and therefore no longer accessible for being bound through an electrostatic bond to the candidate molecules or to the DNA tags.

Aqueous Phase

The aqueous phase of the nanoemulsion used in the invention preferably consist of water and/or of a buffer such as a phosphate buffer like for example PBS («Phosphate Buffer Saline») or a saline solution, notably of sodium chloride.

According to an embodiment, the continuous aqueous phase also includes a thickener such as glycerol, a saccharide, an oligosaccharide or a polysaccharide, a gum or even a protein, preferably glycerol. Indeed, the use of a continuous phase with a higher viscosity facilitates emulsification and consequently allows reduction in the sonication time.

The aqueous phase advantageously includes from 0 to 50% by weight, preferably from 1 to 30% by weight and most particularly from 5 to 20% by weight of thickener.

Of course, the aqueous phase may further contain other additives such as colouring agents, stabilizers and preservatives in a suitable amount.

The proportion of dispersed phase and of aqueous phase is highly variable. However, most often, the nanoemulsions will be prepared with 1 to 50%, preferably 5 to 40% and most particularly 10 to 30% by weight of dispersed phase and 50 to 99%, preferably 60 to 95% and most particularly 70 to 90% by weight of aqueous phase.

Size of the Droplets of the Formulation

The droplets of the formulation defined above generally have a diameter comprised between 20 and 200 nm. This diameter may notably be measured by quasi-elastic scattering of light on a ZetaSizer apparatus from Malvern.

It is possible to obtain droplets with a more specific size by adapting the percentages of the components of the nanoemulsion.

For a formulation comprising droplets with a size comprised between 20 and 40 nm, the use of a formulation comprising at least 5% molar of amphiphilic liquid and:
from 25 to 45% molar of co-surfactant (below 25% molar, the formulation may have stability problems), and/or
from 15 to 50% molar of cationic surfactant, will be preferred.

For a formulation comprising droplets with a size comprised between 40 and 100 nm, the use of a formulation comprising at least 5% molar of amphiphilic liquid and:
from 45 to 50% molar of co-surfactant (below 45% molar, the formulation may have stability problems. Beyond 50%, the transfection efficiency of the formulation is lower), and/or
from 30 to 40% molar of cationic surfactant, (below 30% molar, the transfection efficiency of the formulation is lower. Beyond 40%, the formulation may have stability problems) will be preferred.

For a formulation comprising droplets with a size comprised between 130 and 175 nm, the use of a formulation will be preferred, comprising at least 5% molar of amphiphilic liquid and from 15 to 70% molar of at least one cationic surfactant and:
from 10 to 25% molar, notably from 10 to 15% of co-surfactant.

The molar percentages of amphiphilic liquid, of cationic surfactant and of co-surfactant are relatively to the (amphiphilic lipid/cationic surfactant/co-surfactant/possible fusogenic lipid) assembly.

Tracer

Within the scope of the present invention, by the term of "tracer", is meant a molecule giving the possibility of determining whether the nanoparticle was integrated into a cell. In certain embodiments, said tracer is a magnetic tracer, a radioactive tracer or a fluorophore.

The magnetic tracer may be a gadolinium chelate or a magnetic nanocrystal, such as for example a nanocrystal of iron, manganese oxide or iron-platinum (Fe-Pt).

The radioactive tracer may be a compound comprising a radionuclide, such as for example $^{123}$I, $^{18}$F, $^{11}$C, or a chelate of $^{99m}$Tc or $^{111}$In, or a chelate of metal cations $^{68}$Ga, $^{64}$Cu.

The fluorophore is preferably a lipophilic fluorophore. Preferably, the fluorophores used absorb and emit in the visible or near infrared range. The selected fluorophore is adapted to the type of application of the method: in-vivo or in-vitro. In the case of in-vivo applications, it is possible to resort to in-vivo fluorescence imaging. For this non-invasive imaging, the preferred fluorophores absorb and emit in the near infrared. Indeed, in order that the excitation light and the light emitted by the fluorophore may better cross the tissue, fluorophores absorbing and emitting in the near infrared should be used, i.e. at a wavelength comprised between 640 and 900 nm. During in-vitro applications, for which imaging methods are applied, such as fluorescence microscopy or cytometry of the FACS (Fluorescence Activating Cell Sorting) type, fluorophores are generally applied which are excited with visible wavelengths, typically comprised between 450 nm and 650 nm. These are notably hydrophilic cyanins or FITC (Fluorescein isothiocyanate). These fluorophores may be encapsulated in the lipid core of the nanoparticles or, when they are hydrophilic be localised at their surface.

As a lipophilic fluorophore, mention may for example be made of the compounds described in chapter 13 ("Probes for Lipids and Membranes") of the InVitrogen catalogue (The Molecular Probes® Handbook, a guide to fluorescent probes and labeling technologies, 11$^{th}$ Edition, 2010). More specifically, mention may notably be made as a fluorophore, of indocyanine green (ICG), analogs of fatty acids, and the phospholipids functionalised with a fluorescent group such as the fluorescent products sold under the commercial names of Bodipy (R) such as Bodipy (R) 665/676 (Ex/Em.); lipophilic derivatives of carbocyanins such as 1.1'-dioctadecyl-3,3,3',3'-tetramethylindodicarbocyanin perchlorate (DiD), for example sold under reference D-307, 3,3'-dihexadecyloxacarbocyanin perchlorate (DiO), for example sold under reference D1125, 1,1'-dihexadecyl-3,3,3',3'-tetramethylindocarbocyanin perchlorate (Dil), for example sold under reference D384; the fluorescent probes derived from sphingolipids, from steroids or lipopolysaccharides such as the products sold under the commercial names BODIPY® TR ceramides, BODIPY® FL C5-lactosylceramide, BODIPY® FL C5-ganglioside, BODIPY® FL cerebrosides; amphiphilic derivatives of cyanins, rhodamines, fluoresceins or cumarins such as octadecyl rhodamine B, octadecyl fluorescein ester and 4-heptadecyl-7-hydroxycumarin; and diphenylhexatriene (DPH) and derivatives thereof; the whole of these products being sold by Invitrogen.

According to a preferred embodiment of the invention, the fluorophore is indocyanine green, 1,1'-dioctadecyl-3,3,3',3'-tetramethylindodicarbocyanine perchlorate, 3,3'-dihexadecyloxacarbocyanine perchlorate, or 1,1'-dihexadecyl-3,3,3',3'-tetramethylindocarbocyanine perchlorate.

Candidate Molecule

Within the scope of the present invention, by the term of "candidate molecule", is meant any molecule capable of generating a phenotype change in a cell and/or a tissue and/or an organ.

In certain embodiments, said candidate molecule is a neutral molecule or a negatively or positively charged molecule. Preferably, said candidate molecule is negatively charged.

As examples, when the nanoparticle as defined above is an anionic nanoparticle, said candidate molecule is positively charged, or when said nanoparticle as defined above is a cationic nanoparticle, said candidate molecule is negatively charged.

In certain embodiments, said candidate molecule is a chemical molecule. Preferably, said chemical molecule is a pharmaceutical active ingredient, a biomolecule, a useful agent for physical therapies, or a radioactive agent. Preferably, said chemical molecule is a therapeutic agent.

From the pharmaceutical active ingredients of interest as therapeutic agents, mention may in particular be made of agents used in treating AIDS, agents used in the treatment of heart diseases, analgesics, anaesthetics, anorectics, anthelmintics, anti-allergics, anti-anginal agents, anti-arrhythmic agents, anticholinergics, anticoagulants, anti-depressants, antidiabetics, antidiuretics, anti-emetics, anticonvulsants, antifungal agents, antihistaminics, antihypertensives, anti-inflammatories, anti-migraine agents, antimuscarinic agents, antimycobacterial agents, anticancer agents, including anti-Parkinson agents, antithyroid agents, antiviral agents, astringents, blocking agents, blood products, blood substitutes, cardiac inotropes, cardiovascular agents, central nervous system agents, chelators, chemotherapy agents, haematopoietic growth factors, corticosteroids, antitussive agents, dermatological agents, diuretics, dopaminergics, inhibitors of elastase, endocrine agents, ergot alkaloids, expectorants, gastrointestinal agents, genitourinary agents, growth hormone triggering factor, growth hormones, haematological agents, haematopoietic agents, hemostatics, hormones, immunosuppressors, interleukins, analogs of interleukins, lipid regulation agents, gonadotropin releasing agents, muscle relaxants, narcotic antagonists, nutrients, nutritive agents, oncological therapies, organic nitrates, vagomimetics, prostaglandins, antibiotics, renal agents, respiratory agents, sedatives, sex hormones, stimulants, sympathomimetics, systemic anti-infection agents, tacrolimus, thrombolytic agents, thyroid agents, treatments for attention disorders, vasodilators, xanthins, agents reducing cholesterol. Particularly targeted are anti-cancer agents such as Taxol (Paclitaxel), Doxorubicin and Cisplatin.

Among biomolecules, mention may be made of proteins, peptides, antibodies, saccharides and nucleic acids.

Among agents useful for physical therapies, mention may be made of compounds useful for thermotherapy, compounds releasing singlet oxygen after excitation with light useful for phototherapy (i.e., photo-sensitisers) and radioactive agents.

Among radioactive agents, mention may notably be made of radioactive isotopes.

Among photo-sensitisers, mention may notably be made of those belonging to the class of tetrapyrroles like porphyrins, bacteriochlorins, phthalocyanins, chlorins, purpurins, porphycenes, pheophorbides or further those belonging to the class of texaphyrins or hypericins. Among first generation photo-sensitisers, mention may be made of hemato-porphyrin and of a mixture of hemato-porphyrin derivatives (HpD) (sold under the trade name of Photofrin® by Axcan Pharma). Among second generation photo-sensitisers, mention may be made of meta-tetra-hydroxyphenyl chlorin (mTHPC; trade name Foscan®, Biolitec AG) and the monoacid derivative of ring A of benzoporphyrin (BPD-MA sold under the trade name of Visudyne® by QLT and Novartis Ophthalmics). The formulations of second generation photo-sensitisers which associate with these photo-sensitisers a molecule (lipid, peptide, sugar etc . . . ) described as a carrier which allows their selective transport at tumoral tissue are called third generation photo-sensitisers.

In an embodiment, said negatively charged candidate molecule is a nucleic acid. Preferably, said nucleic acid comprises or consists in a nucleotide sequence which may modulate the RNA interfering mechanisms. In certain embodiments, said nucleotide sequence comprises modified nucleotides, such as inosine.

By "nucleotide sequence which may modulate RNA interfering mechanisms", is meant an antisense nucleic acid which binds to an RNA target via RNA-RNA, RNA-DNA or protein-RNA interactions (Egholm et al., 1993, Nature, 365: 566) and alters the activity of the RNA target (for a review, see Stein and Cheng, 1993, Science, 261, 1004 and Woolf et al., U.S. Pat. No. 5,849,902). Generally, a contiguous sequence of the antisense nucleic acid is complementary to a target sequence. However, in certain embodiments, the antisense nucleic acid may be bound to a substrate so that the substrate forms a loop or a hairpin structure, and/or the antisense nucleic acid may fold back so as to form a loop or a hairpin structure. Thus, (i) the antisense nucleic acid may be complementary to 2, 3, 4, 5, 6, 7, 8, 9, 10, or more non-contiguous substrate sequences, and/or (ii) 2, 3, 4, 5, 6, 7, 8, 9, 10, or more portions of a non-contiguous sequence of the antisense nucleic acid may be complementary to the target sequence (for example, see Crooke, 2000, Methods Enzymol., 313: 3-45).

The antisense nucleic acid enters a cell route which is commonly called RNA interfering route (RNAi). The term of "interference by RNA" refers to selective intracellular degradation of RNA also known under the name of "gene silencing". The RNAi also includes repression of the translation by the small interfering RNAs (siRNA). The iRNA may for example be initiated by introducing a double-strand of long RNA (dsRNA) or siRNA.

In certain embodiments, said nucleotide sequence which may modulate RNA interfering mechanisms is:
- a small interfering RNA (siRNA) ("short-interfering RNA" or "small interfering RNA"),
- a blocked nucleic acid ("Locked Nucleic Acid" (LNA)), or
- a microRNA (miRNA) ("MicroRNA2 or "miRNA"), or
- a long double strand RNA (dsRNA) ("Long double-stranded RNA").

A "short interfering RNA2 or "siRNA" is an RNA duplex of nucleotides which is intended to target a gene of interest. An RNA duplex refers to a structure formed by complementary pairing between two regions of the RNA molecule. In certain embodiments, the length of the duplex of the siRNA is comprised between 15 nucleotides and 50 nucleotides, preferably between 20 nucleotides and 35 nucleotides, still preferably between 21 nucleotides and 29 nucleotides. In certain embodiments, the duplex may be long with at least 15, 16, 17, 18, 19, 20, 21, 22, 23, 24, 25, 26, 27, 28, 29, 30, 31, 32, 33, 34, 35, 40, 45, 50 nucleotides. In certain embodiments, the duplex may be long with at most 45, 40, 35, 34, 33, 32, 31, 30, 29, 28, 27, 26, 25, 24, 23, 22, 21, 20, 19, 18, 17, 16, 15 nucleotides. The duplex portion of the siRNA may be part of a hairpin structure. In addition to the duplex portion, the hairpin structure may contain a loop between both sequences forming the duplex. The loop may vary in length. In certain embodiments, the length of the loop is of 5, 6, 7, 8, 9, 10, 11, 12, or 13 nucleotides. Two deoxythymidines are generally added in part 3' of each of its strands in order to increase the stability thereof. Thus, an siRNA for which deoxythymidines have been grafted to its 3' parts is not outside the definition of an siRNA according to the present application. An siRNA allows reduction in the expression of a target protein by interference with the messenger RNA coding for this protein.

The term of "Long double-stranded RNA" (dsRNA) refers to an oligoribonucleotide or a polyribonucleotide, either modified or not, as well as in its fragments or portions, of genomic or synthetic origin or derived from the expression of an expression vector, which may be partly or totally double-stranded and for which the ends may be blunt ("blunt ended") or contain leaving ends in 5' and in 3', and which may also have a hairpin shape. In certain embodiments, the dsRNA has a size comprised between 250 bp to 2000 bp, preferably between 300 bp and 1000 bp. In certain embodiments, the dsRNA has a size of at least 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950, 1000, 1500 bp. In certain embodiments, the dsRNA has a size of at most 3000, 2500, 2000, 1500, 1000, 950, 900, 850, 800, 750,700, 650, 600, 550, 500, 450, 400, 350, 300 bp.

In an embodiment, said nucleotide sequence is a locked nucleic acid.

A locked nucleic acid is a nucleotide sequence of single-stranded RNA and/or DNA, for which at least one of the nucleic acids contains a methylene bridge between the hydroxyl in position 2 and the carbon atom 4 of the ribose. This is a synthetic nucleotide sequence. A locked nucleic acid is an inhibitor of microRNA and allows regulation of the expression of one or more target proteins for which the mRNAs were interfering with the RNA sequences from said microRNA. The regulation is most often removal of the inhibition of expression of proteins.

In an embodiment, said nucleotide sequence is a microRNA.

A microRNA is a nucleotide sequence of single-stranded RNA (of the order of 100 bases). This is a synthetic nucleotide sequence.

A microRNA allows regulation of the expression of one or more target proteins by interference with one or more mRNAs respectively coding for these proteins. The regulation is most often an inhibition of the expression of the proteins.

Single DNA Tag

By "single DNA tag", is meant a specific double-stranded or single-stranded nucleotide sequence of a candidate molecule.

In certain embodiments, said single DNA tag consists in a sequence of single-stranded DNA with at least 50, 55, 60, 65, 70, 75, 80, 85, 90, 95, 100 nucleotides, or of at most 100, 95, 90, 85, 80, 75, 70, 65, 60, 55, 50 nucleotides. In certain embodiments, said single DNA tag consists in a sequence of double-stranded DNA with at least 50, 55, 60, 65, 70, 75, 80, 85, 90, 95, 100 base pairs (bp), or with at most 100, 95, 90, 85, 80, 75, 70, 65, 60, 55, 50 bp.

Preferably, in the library of nanoparticles according to the invention or in the screening methods according to the invention, said single DNA tag consists in a sequence of DNA, preferably double-stranded DNA, with at least 50 nucleotides or by consisting in, on a strand and in the 5'-3' sense:

a first sequence of at least 20 nucleotides common to all the single DNA tags of the library,
a single sequence of at least 10 nucleotides specific to the candidate molecule as defined above,
a second sequence of at least 20 nucleotides common to all the single DNA tags of the library.

Said first and second sequences are notably useful for amplifying and/or sequencing said single DNA tag. For this purpose, it is preferable that said first or second sequences have a nucleotide sequence which does not exist in the genome of the cell, of the tissue or of the organism from which stems the cell put into contact with the library of nanoparticles. For example, (i) when the cell put into contact with the library of nanoparticles is a human cell, said first and second sequences are not part of the human genome; (ii) when the cell put into contact with the library of nanoparticles is a cell of an animal, such as a rodent (rat, mouse) cell, said first and second sequences are not part of the genome of said animal; (iii) when the cell put into contact with the library of nanoparticles is a cell of a plant, said first and second sequences are not part of the genome of said plant. Preferably, said first or second sequences comprise at least 1, 2, 3, 4, 5, 6, or more of modified nucleotides. For example, said first and second sequences comprise at least 1, 2, 3, 4, 5, 6, or more of inosine.

In certain embodiments, said first and second sequences are identical or different, preferably said first and second sequences are different. This gives the possibility of using a single pair of primers for the whole of the tags, during the amplification step. In certain embodiments, said first and second sequences have a length of at least 20, 25, 30, 35, 40, 45, 50 nucleotides, or of at most 50, 45, 40, 35, 30, 25, 20 nucleotides.

By "single sequence of at least 10 nucleotides specific to the candidate molecule", is meant a sequence associated in silico to a determined candidate molecule. Thus, in a library of nanoparticles, each candidate molecule is associated with a single sequence of at least 10 nucleotides and may be identified by means of this single sequence contained in the single DNA tag. In certain embodiments, said single sequence specific to the candidate molecule has a length of at least 10, 11, 12, 13, 14, 15, 16, 17, 18, 19, 20, 21, 22, 23, 24, 25, 30, 35, 40, 45, 50 nucleotides, or at most 50, 45, 40, 35, 30, 25, 24, 23, 22, 21, 20, 19, 18, 17, 16, 15, 14, 13, 12, 11, 10 nucleotides.

In certain embodiments, the single sequence has a nucleotide sequence which does not exist in the genome of the cell, of the tissue or of the organism from which stems the cell put into contact with the library of nanoparticles. For example, (i) when the cell put into contact with the library of nanoparticles is a human cell, said single sequence is not part of the human genome; (ii) when the cell put into contact with the library of nanoparticles is a cell of an animal, such as a rodent cell (rat, mouse), said single sequence is not part of the genome of said animal; (iii) when the cell put into contact with the library of nanoparticles is a cell of a plant, said single sequence is not part of the genome of said plant. Preferably, said single sequence comprises at least 1, 2, 3, 4, 5, 6, or more of modified nucleotides. For example, said single sequence comprises at least 1, 2, 3, 4, 5, 6, or more of inosine.

The synthesis of said single DNA tags may be carried out with methods known to one skilled in the art.

Biological Ligand for Targeting a Cell and/or an Organ

The targeting biological ligand may for example be an antibody, a peptide, a saccharide, an aptamer, an oligonucleotide or a compound like folic acid.

According to an embodiment, said targeting biological ligand is grafted at the surface with an amphiphilic compound, notably with the co-surfactant, of the droplet of the formulation in the form of a nanoemulsion comprising a continuous aqueous phase and at least one dispersed phase as defined above. The nanoemulsion then comprises a grafted co-surfactant. In this case, the co-surfactant plays the role of a spacer allowing accommodation of the targeting biological ligand at the surface. For example, when the biological ligand is a peptide comprising one or more cysteines, the grafting to the alkylene oxide chain of the surfactant may be ensured by thiol-maleimide coupling.

Localisation of the Components of the Nanoparticles

When the Nanoparticle is Inorganic

When the nanoparticle is inorganic, e.g. when the nanoparticle is a gold nanoparticle or a magnetic nanoparticle or a semi-conducting material nanocrystal, the candidate molecule, the tracer and the single DNA tag as defined above are localised at the surface of said inorganic nanoparticle. Preferably, the candidate molecule, the tracer and the single DNA tag as defined above are complexed in a non-covalent way at the surface of said inorganic nanoparticle.

When the Nanoparticle is Organic

When the nanoparticle is organic, e.g. when the nanoparticle is a cation vector, the candidate molecule, the tracer and/or the single DNA tag as defined above are localised at the surface of said organic nanoparticle and/or are encapsulated in said organic nanoparticle, depending on the nature of the candidate molecule, of the tracer and of the single DNA tag.

In certain embodiments, (i) when said nanoparticle is a droplet of a formulation in the form of a nanoemulsion comprising a continuous aqueous phase and at least one dispersed phase as defined above and (ii) when said candidate molecule is negatively charged:

said negatively charged candidate molecule and said single DNA tag are maintained at the surface of the droplets of the dispersed phase of the formulation by means of the electrostatic interactions with the cationic surfactant, i.e., they are therefore localised at the surface of the droplets, at the crown of the droplets, on the hydrophilic side of the crown, the tracer as defined above is localised in the core of the droplets.

Accordingly, in a preferred embodiment, the droplets of the formulation according to the invention are organised in the form of a core-crown, wherein:

the core comprises:
  the solubilizing lipid,
  the optional oil,
  the tracer,
the crown comprises:
  the amphiphilic lipid,
  the cationic surfactant,
  the co-surfactant (optionally grafted with a molecule of interest),
  the nucleotide sequence which may modulate the interfering RNA endogenous mechanisms,
  the single DNA tag,
  the optional fusogenic lipid,
  the optional surfactant of formula (I),
  the optional targeting biological ligand.

In addition to the optional binding of the siRNAs to the deoxythymidines mentioned above, said nucleotide sequences are not chemically modified and they are not denaturated. In particular, said nucleotide sequences are not covalently bound to the nanoparticles. Notably, said nucleotide sequences are not covalently bound either to the co-surfactant, or to the amphiphilic lipid, or to the optional imaging agent. Indeed, said nucleotide sequences are only bound to the droplets of the nanoemulsion by electrostatic interactions with the cationic surfactants. This is highly advantageous since said nucleotide sequences, once released in their site of action, are not denaturated and may play the expected role. Further, it is not necessary to prepare derivatives of nucleotide sequences, which is costly. The nucleotide sequences available commercially may therefore be complexed to the droplets without any modification beforehand.

In certain embodiments, (i) when said nanoparticle is a droplet of a formulation in the form of a nanoemulsion comprising a continuous aqueous phase and at least one dispersed phase as defined above and (ii) when said candidate molecule is a chemical molecule, the droplets of the formulation according to the invention are organised in the form of a core-crown, wherein:

the core comprises:
  the solubilizing lipid,
  the optional oil,
  the tracer,
  the chemical molecule if it is lipophilic,
the crown comprises:
  the amphiphilic lipid,
  the cationic surfactant,
  the co-surfactant (optionally grafted with a molecule of interest),
  the chemical molecule if it is amphiphilic,
  the single DNA tag,
  the optional fusogenic lipid,
  the optional surfactant of formula (I),
  the optional targeting biological ligand.

These embodiments further have the following additional advantages, when the candidate molecule is localised at the surface of each nanoparticle:

it is sufficient to prepare a single and same emulsion for forming the nanoparticles, which are then grafted with the different candidate molecules, in order to form the library of nanoparticles;

when the nanoparticle is a droplet in which the fluorophore (and/or DNA tag) is encapsulated, this gives the possibility of limiting the risk of interaction between the fluorophore (and/or the DNA tag) and the candidate molecule, the latter being localised at the surface of the droplet.

LIBRARY OF NANOPARTICLES

In certain embodiments, the library of nanoparticles comprises or consists in at least 2, 10, 50, 100, 250, 500, 1000, 2500, 5000, 7500, 10,000, 12,500, 15,000, 20,000, 30,000, 50,000, 75,000, 100,000, or more nanoparticles as defined above. In certain embodiments, said library comprises or consists in a number of nanoparticles comprised between 2 and 100,000, preferably between 500 and 50,000, still preferably between 1000 and 15,000.

In certain embodiments, said library of nanoparticles comprises or consists in a number of nanoparticles at least equal to the number of candidate molecules present in a collection of molecules commercially available, or at least equal to a number of functionally related candidate molecules (e.g. candidate molecules having the same target, for example inhibitors of a same class of enzyme, of a same metabolic route, or of a same gene, functionally related candidate molecules have the same mechanism of action on a metabolic route or on a signaling route), i.e., there exists at least one copy of each type of nanoparticle, the type being defined by the combination of the candidate molecule, the tracer and the single DNA tag.

In certain embodiments, said library of nanoparticles comprises or consists in at least 1, 2, 10, 50, 100, 250, 500, 1000, 2500, 5000, 7500, 10,000, 20,000, 50,000, 75,000, 100,000 type(s) of nanoparticles, each type of nanoparticles being present in a number of copies at least equal to 10, 50, 100, 500, 1000, 2000, 5000, 7500, 10,000, 15,000, 20,000 nanoparticles.

As non-limiting examples of a collection of candidate molecules, mention may notably be made of the collection of 1292 siRNAs from Qiagen targeting 646 kinases (Human Kinase siRNA set V1.0; Ref. 1027091), or the collection of 2375 siRNAs from Qiagen targeting 1183 genes involved in cancers (Human Cancer siRNA set V2.0), or the collection of 278 siRNAs targeting 139 genes involved in cancers (Human Cancer siRNA set V1.0; Ref. 1022171), or the collection of 91,800 siRNAs from Qiagen targeting 22,950 human genes (Human Genome Wide siRNA set), or the collection of 982 LNAs from Exiqon targeting all the known human miRNAs (miRCURY LNA Human microRNA Inhibitor Library; Ref. 190102-2).

As a non-limiting example, said library of nanoparticles comprises or consists in 1292 nanoparticles, each nanoparticle comprising one of the siRNAs of the collection of 1292 siRNAs from Qiagen targeting 646 kinases, a tracer and a single DNA tag specific to said siRNA; or said library of nanoparticles comprises or consists in 2375 nanoparticles, each nanoparticle comprising one of the siRNAs of the collection of 2375 siRNAs from Qiagen targeting 1183 genes involved in cancers, a tracer and a single DNA tag specific to said siRNA; or said library of nanoparticles comprises or consist in 278 nanoparticles, each nanoparticle comprising one of the siRNAs of the collection of 278 siRNAs targeting 139 genes involved in cancers, a tracer and a single DNA tag specific to said siRNA; or said library of nanoparticles comprises or consists in 91,800 nanoparticles, each nanoparticle comprising one of the siRNAs of the collection of 91,800 siRNAs from Qiagen targeting 22,950 human genes, a tracer and a single DNA tag specific to said siRNA; or said library of nanoparticles comprises or consists in 982 nanoparticles, each nanoparticle comprising one of the LNAs of the collection of 982 LNAs from Exiqon targeting all the known human miRNAs, a tracer and a single DNA tag specific to said LNA.

Said library of nanoparticles may also comprise or consist in at least 1, 2, 3, 4, 5, 10, 15, 20, 50, 100, 500, 1000, 2500, 5000 families of nanoparticles, each family comprising at least 2, 3, 4, 5, 10, 15, 20, 25, 50, 100, 200 types of nanoparticles comprising a same tracer and the candidate molecules being functionally related (e.g. candidate molecules with the same target, for example inhibitors of a same class of enzyme, of a same metabolic route, or of a same gene, functionally related candidate molecules have the same action mechanism on a metabolic route or on a signaling route) or being present in a collection of commercially available molecules, such as for example one of the collections mentioned above.

For example, said library of nanoparticles may comprise or consist in two families of nanoparticles, the first family of nanoparticles comprising or consisting in 1292 types of nanoparticles, each type of nanoparticles comprising one of the siRNAs of the collection of 1292 siRNAs from Qiagen targeting 646 kinases, a tracer and a single DNA tag specific to said siRNA; and the second family of nanoparticles comprising 2375 types of nanoparticles, each type of nanoparticles comprising one of the siRNAs of the collection of 2375 siRNAs from Qiagen targeting 1183 genes involved in cancers, a tracer and a single DNA tag specific to said siRNA, it being understood that the tracers of the first and second families of nanoparticles are different.

According to another example, said library of nanoparticles may comprise or consist in five families of nanoparticles, the first family of nanoparticles comprising or consisting in 1292 types of nanoparticles, each type of nanoparticles comprising one of the siRNAs of the collection of 1292 siRNAs from Qiagen targeting 646 kinases, a tracer and a single DNA tag specific to said siRNA; the second family of nanoparticles comprising or consisting in 2375 types of nanoparticles, each type of nanoparticles comprising one of the siRNAs of the collection of 2375 siRNAs from Qiagen targeting 1183 genes involved in cancers, a tracer and a single DNA tag specific to said siRNA; the third family of nanoparticles comprising or consisting in 278 types of nanoparticles, each type of nanoparticles comprising one of the siRNAs of the collection of 278 siRNAs from Qiagen targeting 139 genes involved in cancers, a tracer and a single DNA tag specific to said siARNA; the fourth family of nanoparticles comprising or consisting in 91,800 types of nanoparticles, each type of nanoparticles comprising one of the siRNAs of the collection of 91,800 siRNAs from Qiagen targeting 22,950 human genes, a tracer and a single DNA tag specific to said siRNA, the fifth family of nanoparticles comprising or consisting in 982 types of nanoparticles, each type of nanoparticles comprising one of the LNAs of the collection of 982 LNAs from Exiqon targeting all the known human miRNAs, a tracer and a single DNA tag specific to said LNA, it being understood that the tracers of the first, second, third, fourth and fifth families of nanoparticles are different.

CELLS

The cells used in the screening methods according to the invention may be eukaryotic or prokaryotic cells. The cells may be primary cells or immortalized cells. Examples of eukaryotic cells which may be used in the invention are cells of mammals, preferably human cells, or plant cells. Mammalian cells may for example be lymphoid cells, embryo cells, fetal cells, epithelial cells, myeloid cells, tumoural cells, adult or embryo stem cells, cells infected by a virus, a bacterium, a fungus or a parasite. Preferably, the cells are human cells, including those from healthy donors. Still preferably, the cells are tumoural cells or cells infected by a virus. Said tumoral cells may stem from tumours at various evolutionary stages and/or tumours having different sensitivities to anticancer therapies. As a non-limiting example, the tumoural cells may be cells from breast, prostate, brain cancer (neuroblastoma, astrocytoma, oligodendroglioma), kidney, liver cancer (hepatocarcinoma), pancreas, adrenal gland, colon cancer, colorectal cancer, cancer of the ovaries, of the testicles, of the uterus, of the lungs, a carcinoma, a sarcoma, a lymphoma, a myeloma, a haematopoietic cancer, leukaemia, a melanoma.

The plant cells may be cells from a monocotyledonous plant or a dicotyledonous plant. For example, the plant cells may stem from the leaves, from the stem, from the root, from an embryo, from a shoot.

The cells used in the screening methods according to the invention may be suspended cells, adherent cells in a two-dimensional culture or in a three-dimensional culture.

PREPARATION OF THE LIBRARY OF NANOPARTICLES

Step a0) may be carried out according to the following steps: (i) preparation and composition of a formulation in the form of a nano-emulsion, comprising a continuous aqueous phase and at least one dispersed phase, (ii) encapsulation or complexation of the tracer, (iii) complexation of the DNA tag, (iv) encapsulation or complexation of the candidate molecule. The steps (i) to (iv) may notably be carried out according to the methods described in Example 1 in paragraphs 1.1, 1.5, 1.4 and 1.2, respectively.

PUTTING THE CELLS IN CONTACT WITH A LIBRARY OF NANOPARTICLES

The putting of the cells into contact with the library of nanoparticles as described above has the purpose of allowing at least one nanoparticle to be integrated into the cells. It may be carried out by methods known to one skilled in the art. It is also based on the fact that the cells are put into contact with the library of nanoparticles without any preliminary ordering of the candidate molecules. Thus, the cells are for example cultivated in a suitable medium, and then collectively transfected with the library of nanoparticles, for example in a 1/1 (1 nanoparticle/1cell) ratio. According to another example, each nanoparticle of the library is deposited on a support, for example in a well of a cultivation plate, and the cells are added onto said support.

Preferably, said contacting consists in a step for transfecting the cells with the library of nanoparticles as described above.

Step a) for putting the cells in contact with the library of nanoparticles may for example be carried out for at least 30 min, 1 h, 2 h, 3 h, 4 h, 5 h, 6 h, 7 h, 8 h, 9 h, 10 h, 12 h, 18 h, 24 h, 36 h, 48 h, 3 d, 4 d, 5 d, 6 d, 7 d, 8 d, 9 d, or 10 d, and/or at most 10 d, 9 d, 8 d, 7 d, 6 d, 5 d, 4 d, 3 d, 48 h, 36 h, 24 h, 18 h, 12 h, 10 h, 8 h, 7 h, 6 h, 5 h, 4 h, 3 h, 2 h, 1 h or 30 min.

The step a) for putting the cells in contact with the library of nanoparticles may for example be carried out at a temperature of at least 20, 21, 22, 23, 24, 25, 26, 27, 28, 29, 30, 31, 32, 33, 34, 35, 36, 37, 38, 39, or 40° C., and/or of at most 40, 39, 38, 37, 36, 35, 34, 33, 32, 31, 30, 29, 28, 27, 26, 25, 24, 23, 22, 21, or 20° C.

In an embodiment, when the cells are adherent cells, step a) is followed by a step of trypsination of the cells or of scraping.

SELECTION OF THE CELLS

In the methods according to the invention, the cells are selected according to the two following criteria: (i) integration of the tracer as described above and (ii) presentation of a phenotype of interest.

Identification of the cells having integrated the tracer may be carried out by means of methods known to one skilled in the art.

In an embodiment, when said tracer is a magnetic tracer, the selection of the cells having integrated said magnetic tracer is carried out by magnetic cell sorting (MACS® for "Magnetic Activated Cell Sorting").

In an embodiment, when said tracer is a fluorophore, the selection of the cells having integrated said fluorophore is carried out by flow cytometry.

The identification of the cells having a phenotype of interest may be carried out by means of methods known to one skilled in the art. Preferably, identification of the cells having a phenotype of interest is carried out by flow cytometry.

In an embodiment, the identification of the cells having integrated the tracer is carried out before identifying the cells having a phenotype of interest. In another embodiment, the identification of the cells having integrated the tracer and the identification of the cells having a phenotype of interest are carried out simultaneously.

Non-limiting examples of a phenotype of interest are notably apoptosis, cell proliferation, differentiation, the expression of a cancer maker, such as for example the expression of the prostate specific antigen (PSA), resistance or sensitivity to a therapeutic agent, for example a chemotherapy agent, the resistance or sensitivity to an infectious agent, preferably to a virus, the resistance or sensitivity to an environmental stress, such as for example resistance or sensitivity to drought or to an insect.

The phenotypes of interest may be studied without any preliminary marking or with marking with a fluorescent reporter gene or else further after marking with a fluorescent antibody. Identification of the proliferation of the cells may notably be achieved by marking with propidium iodide, EdU, or Hoechst 33342. Identification of apoptosis of the cells may notably be achieved by Annexine V-FITC marking or by so called TUNEL ("Terminal deoxynucleotidyl transferase dUTP Nick End Labelling") marking or by analysis of activation of caspases.

IDENTIFICATION OF THE CANDIDATE/MOLECULE OF INTEREST

In the method according to the invention, the identification in step c) of the candidate molecules having been integrated in step b) is achieved by identifying the single DNA tag sequence. Indeed, as each candidate molecule is associated with a single DNA tag, by identifying said single DNA tag, it is possible to determine which candidate molecule was integrated into the cells.

Identification of the DNA tag is achieved after (i) extraction of the DNA from the cells selected in step b), (ii) amplifying the DNA extracted in step (i) with complementary universal primers of the first and second sequences with at least 20 nucleotides of said single DNA tags, as defined above, and sequencing of the amplified DNA, or (iib) sequencing of the DNA extracted in step (i).

The DNA extraction step (i) may be achieved with methods known to one skilled in the art.

In step (ii), the amplification may be achieved by using polymerase chain reaction conventional techniques (PCR).

In certain embodiments, the amplification in step (ii) comprises an initial denaturation step followed by denaturation-hybridization-elongation cycles and by a final extension step.

The initial denaturation step may be achieved under temperature conditions ranging from 90° C. to 105° C., for 15 s to 15 min, preferably from 92° C. to 102° C., still preferably from 95° C. to 100° C. Preferably, the initial denaturation step is carried out for 1 min to 15 min, still preferably for 2 min to 12 min, still preferably for 5 min to 10 min.

Each denaturation-hybridization-elongation cycle includes a denaturation phase under heating conditions, followed by a phase for hybridization of the primers, produced under conditions allowing hybridization of the primers with the single DNA tag to be amplified, and an elongation phase produced under conditions allowing the polymerase to synthesize an extension product from each primer having been hybridized with the DNA tag to be amplified.

The denaturation phase may be achieved between 90° C. and 105° C., preferably between 92° C. and 100° C., still preferably between 94° C. and 98° C., for 10 s to 4 min, preferably for 10 s to 2 min, still preferably for 15 s to 1 min.

The hybridization phase, i.e., the hybridization phase of the primers, may be achieved between 35° C. and 70° C., preferably between 40° C. and 65° C., still preferably between 45° C. and 60° C., for 10 s to 2 min, preferably for 20 s to 1.5 min, still preferably for 25 sec to 45 sec.

The elongation phase may be achieved between 40° C. and 80° C., preferably between 50° C. and 75° C., still preferably between 60° C. and 72° C., for 10 s to 5 min, preferably for 20 s to 3 min, still preferably for 25 s to 1 min.

The denaturation-hybridization-elongation steps may be repeated for 30 to 60 cycles, preferably for 35 to 45 cycles.

The final extension step may be achieved between 40° C. and 80° C., preferably between 50° C. and 75° C., still preferably between 60° C. and 72° C., for 1 min to 10 min, preferably for 3 min to 8 min, still preferably for 4 min to 6 min.

The sequencing in steps (ii) and (iib) may be carried out by using conventional sequencing techniques.

Preferably, the sequencing step (iib) is carried out on third generation sequencers which allow sequencing of a single DNA molecule, e.g. by using the Pacific Bioscience® method, the ion torrent® method, the Oxford nanopore® method, the so called "optipore" method (Noblegen BioSciences). The sequencing in steps (ii) and (iib) therefore allows identification of the single sequence of at least 10 nucleotides of each DNA tag.

INDIVIDUAL SCREENING OF CANDIDATE MOLECULES

In the screening methods according to the invention, it is possible that the cells integrate several nanoparticles, this leading to the identification in step c) of several candidate molecules as being responsible for the phenotype of interest. Thus, in order to make sure that all the identified candidate molecules are really responsible for the phenotype of interest, the screening methods according to the invention may therefore, after step c), further comprise an individual screening step of the identified candidate molecules in step c).

This individual screening step is carried out by achieving a second cycle of steps a) to c), it being understood that the contacting of the cells in step a) is achieved with a nanoparticle comprising a tracer, a fluorophore and the candidate molecule identified in step c).

FORMULATION IN A PHARMACEUTICAL COMPOSITION

The screening method for a molecule of interest according to the invention may further comprise after step c), or after the individual screening step when the latter is present, one or several additional steps consisting of formulating said molecule of interest in a pharmaceutical composition with a pharmaceutically acceptable carrier.

By "pharmaceutically acceptable carrier", is meant a carrier adapted for a use in contact with human or animal cells, without inducing toxicity, irritation, or undue allergic response. Non-limiting examples of pharmaceutically acceptable carriers notably include a physiological solution or liposomes, microparticles, microcapsules or transport systems based on lipids. The liposomes, microparticles, microcapsules and transport systems based on lipids are pharmaceutically acceptable carriers particularly suitable for being formulated with nucleic acids.

DISEASE/PHENOTYPE FEATURE

In certain embodiments, the disease is a cancer, an infection or a cardiovascular disease.

Preferably, the cancer is selected from breast, prostate, brain cancer (neuroblastoma, astrocytoma, oligodendroglioma), kidney, liver cancer (hepatocarcinoma), pancreas, adrenal gland, colon cancer, colorectal cancer, ovary, testicle, uterus, lung cancer, a carcinoma, a sarcoma, a lymphoma, a myeloma, a haematopoietic cancer, leukaemia or a melanoma. Preferably the disease is prostate cancer.

Preferably, the infection is selected from a bacterial, parasite or viral infection. Preferably, the infection is a viral infection.

The cardiovascular disease is selected from hypertension, acute coronary syndrome, atherosclerosis, vascular calcification, or cerebrovascular stroke.

The term of "phenotype feature" refers to the appearance or to another feature of an organism resulting from the interaction of the genome of said organism with the environment. In certain embodiments, the phenotype feature is selected from apoptosis, cell proliferation, resistance or sensitivity to a therapeutic agent, for example to a chemotherapy agent, resistance or sensitivity to an infectious agent, preferably a virus, resistance or sensitivity to an environmental stress, such as for example resistance or sensitivity to drought, to cold, to frost, to high temperatures, resistance or sensitivity to an insect, resistance or sensitivity to a herbicide, a yield, size.

IDENTIFICATION OF THE BIOMARKER OF THE DISEASE OR OF THE PHENOTYPE FEATURE

In the screening method for a biomarker of a disease or of a phenotype feature according to the invention, the identification in step d) of the biomarker of the disease or of the phenotype feature is achieved by identifying the target of the candidate molecule identified in step c).

By "target", is meant a gene, an RNA or a protein for which the expression is modulated by a candidate molecule.

In so far that the modulation of said target is responsible for the phenotype of interest, and therefore for the disease or the phenotype feature, said target is therefore identified as being a biomarker of said disease or of said phenotype feature.

DEFINITIONS

Within the scope of the present invention, by the term of "nanoparticle" is meant a particle of less than 1 micron in diameter. In certain embodiments, said nanoparticle has an average diameter of at least 10, 20, 30, 40, 50, 60, 70, 80, 90, 100, 150, 200, 250, 300 nm or of at most 300, 250, 200, 150, 100, 90, 80, 70, 60, 50, 40, 30, 20, 10 nm. In certain embodiments, said nanoparticle has an average diameter comprised between 10 nm and 500 nm, preferably between 20 nm and 200 nm, still preferably between 50 and 150 nm.

Within the scope of the present application, by the term of "nanoemulsion" is meant a composition having at least two phases, generally an oily phase and an aqueous phase, in which the average size of the dispersed phase is less than 1 micron, preferably from 10 to 500 nm and in particular from 20 to 200 nm, and most preferentially from 50 to 200 nm (see articles C. Solans, P. Izquierdo, J. Nolla, N. Azemar and M. J. Garcia-Celma, *Curr Opin Colloid In,* 2005, 10, 102-110).

In the sense of the present application, the expression of "dispersed phase" means droplets comprising the optional oil/cationic surfactant(s)/solubilizing lipid/amphiphilic lipid/co-surfactant/optional surfactant of formula (I)/possible fusogenic lipid/the candidate molecule/the fluorophore/the single DNA tag. The dispersed phase is generally free of aqueous phase.

The term of "droplet" encompasses both droplets of liquid oil strictly speaking as well as solid particles from emulsions of the oil-in-water type in which the dispersed phase is solid. In the latter case, this is also often referred to as a solid emulsion.

The term of "lipid" designates within the scope of this discussion, the whole of the fats or substances containing fatty acids present in the fats of animal origin and in plant oils. These are hydrophobic or amphiphilic molecules mainly consisting of carbon, hydrogen and oxygen and having a density below that of water. The lipids may be in the solid state at room temperature (25° C.), like in waxes, or liquid like in oils.

The term of "phospholipid" is aimed at lipids having a phosphate group, notably phosphoglycerides. Most often, phospholipids include a hydrophilic end formed by chains of fatty acids. Among phospholipids, mention will in particular be made of phosphatidylcholine, phosphatidyl ethanolamine, phosphatidyl inositol, phosphatidyl serine and sphingomyelin.

The term of «lecithin» designates phosphatidylcholine, i.e. a lipid formed from a choline, a phosphate, a glycerol and two fatty acids. It more widely covers phospholipids extracted from living organisms, of plant or animal origin, in so far that they in majority consist of phosphatidylcholine. These lecithins generally form mixtures of lecithins bearing different fatty acids.

The term of «fatty acid» is meant to designate aliphatic carboxylic acids having a carbon chain of at least 4 carbon atoms. Natural fatty acids have a carbon chain from 4 to 28 carbon atoms (generally an even number). One refers to a long chain fatty acid for a length from 14 to 22 carbons and to a very long chain fatty acid if there are more than 22 carbons.

By the term of «surfactant» are meant compounds with an amphiphilic structure which gives them particular affinity for interfaces of the oil/water and water/oil type, which gives them the capability of lowering free energy of the these interfaces and of stabilizing dispersed systems.

By the term of «co-surfactant» is meant a surfactant acting in addition to a surfactant for further lowering the energy of the interface.

The term of «hydrocarbon chain» is meant to designate a chain consisting of carbon and hydrogen atoms, either saturated or unsaturated (double or triple bond). The preferred hydrocarbon chains are alkyls or alkenyls.

The term of «alkylene» is meant to designate a linear or branched, saturated preferably linear hydrocarbon aliphatic divalent group.

The invention will be described in more detail by means of the appended figures and of the examples which follow.

FIGURES

FIG. 1 illustrates a diagram illustrating the core/crown structure of a droplet of a formulation in the form of a nano-emulsion, comprising a continuous aqueous phase and at least one dispersed phase, as defined in the invention, and comprising a nucleotide sequence which may modulate interfering RNA endogenous mechanisms, a tracer and a single DNA tag. 1 represents the continuous aqueous phase, 2 the crown (partly) of the droplet and 3 the core (partly) of the droplet. In the crown 2, are illustrated: the amphiphilic lipid (for example a neutral phospholipid such as lecithin), the cationic surfactant (cationic phospholipid DOTAP for example), the co-surfactant for which the poly(ethylene oxide) chain which folds back, is represented in the aqueous phase, the double-strand nucleotide sequence which may modulate the interfering RNA endogenous mechanisms (siRNA for example) and the single DNA tag.

FIG. 2 illustrates an electrophoresis gel revealed under UV made by complexation of siRNA with the formulation B10 with concentrations specified in table 8. The scale and the siRNAs (controls) are on the left.

FIG. 3 gives the results of the amount of SiRNA (ng) obtained by processing the data of the electrophoresis on the software package ImageJ of the electrophoresis gel revealed under UV of FIG. 2.

FIG. 4 illustrates the intensity obtained on a ZetaSizer Malvern apparatus versus the hydrodynamic diameter in nm for free siRNA (comparison) and for three formulations according to the invention obtained by complexation with an N/P ratio: amount of positive charges due to the cationic surfactant in the «premix» formulation (due to charged nitrogen, whence the N of N/P), over the amount of negative charges provided by the siRNAs (due to the phosphorus of siRNA, whence the P of N/P) of 4/1, 8/1 or 16/1.

FIG. 5 represents an electrophoresis gel revealed under UV with from left to right:
  the scale,
  the free siRNA (control)
and then the migrations obtained by complexation of siRNA:
  with formulation B1 (comparative example) (no complexation, the siRNAs are free),
  with the formulation B6 with a ratio of the amount of positive charges due to the cationic surfactant in the formulation over the amount of negative charges brought by the siRNAs, of 8/1 (quantitative complexation),
  with the formulation B6 with a ratio of the amount of positive charges due to the cationic surfactant in the formulation over the amount of negative charge brought by the siRNAs, of 8/1 (quantitative complexation),
  with the formulation B10 with a ratio of the amount of positive charges due to the cationic surfactant in the formulation over the amount of negative charge brought by the siRNAs, of 8/1 (quantitative complexation),
  with lipofectamine (comparative example) (incomplete complexation).

FIG. 6 illustrates an electrophoresis gel revealed under UV of an siRNA/formulation B10 complex just after complexation (T0) and then 15 min, 45 min, 1 h 30 min, 3 h and 6 h after complexation. The scale and the siRNAs (controls) are on the left.

FIG. 7 illustrates the decrease of the fluorescence intensity FITC in % by transfecting the cell lines with:
  Lipofectamine RNAimax (commercial agent),
  the siRNA/formulation B1 complex,
  with the siRNA/formulation B6 complex, the formulation having been kept for 7 months at room temperature before complexation,
  with the siRNA/formulation B6 complex, the formulation having been kept for 12 months at room temperature before complexation,
  with the siRNA/formulation B10 complex, the formulation having been kept for 12 months at room temperature before complexation,
  with an siRNA/formulation of cationic liposomes complex comprising DOTAP (58% wt), DOPE (18% wt), cholesterol (2% wt) and DSPE-PEG3000 (22% wt)) (comparative).

FIG. 8 illustrates the fluorescence intensity (FITC) for 3 cell lines experimentally over expressing the fluorescent protein GFP (green fluorescent protein): U2OS, PC3 and Hela for the siRNA/formulation B10 complex, the siRNA called siGFP being targeted against the mRNA coding for the GFP protein, and for the negative control (cells incubated with a complexed formulation B10 with an siRNA, negative control, i.e., "inert" without any effect on the transcriptome of the cell called siAllStar).

FIG. 9 illustrates an electrophoresis gel revealing the nanoparticles A3/DNA tag/siRNA complexes. The nucleic acids are revealed by means of the reagent, GelRed Nucleic Acid Gel Stain (Interchim, Ref. BY1740)

EXAMPLES

Example 1

Figure 1:
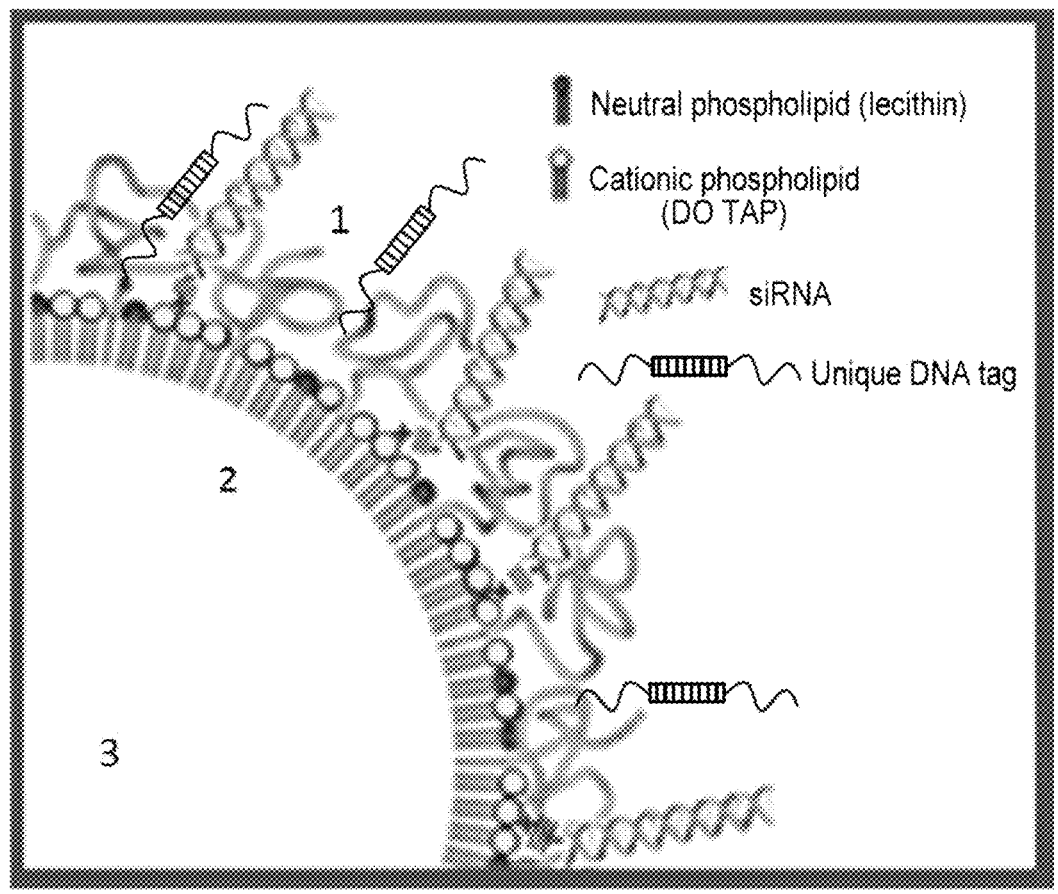

Design and Preparation of Fluorescent Nanoparticles Containing a DNA Tag and an siRNA 1.1. Preparation and Composition of Formulations in the Form of a Nano-Emulsion, Comprising a Continuous Aqueous Phase and at Least One Dispersed Phase The aqueous phase used is a buffer solution PBS 1×.
The suppliers of the compounds are the following:
Lipoid S75-3: Lipoid
Lipoid S75: Lipoid
Lipoid S100-3: Lipoid
DOTAP: Avanti Polar
DOPE: Avanti Polar
MyrjS40: Croda
Suppocire NB: Gattefossé
Soya oil: Croda The hydrodynamic diameter of the droplets of the formulations as well as their zeta potential were measured by quasi-elastic scattering of light with an apparatus of the ZetaSizer type from Malvern. The hydrodynamic diameter of the droplets was measured in a solution of PBS 0.1×, the zeta potential in an aqueous solution of NaCl 0.15 mM.

Sixteen different formulations were made, the compositions of which are indicated in tables 1 to 5.

TABLE 1

| | | A1 (comp.) | A2 | A3 |
|---|---|---|---|---|
| CROWN | Amphiphilic lipid: Lipoid | S75-3 | S75-3 | S75-3 |
| | % wt Lipoid/droplet | 35.29 | 8.83 | 3.53 |
| | % wt Lipoid/crown without PEG | 100 | 25 | 10 |
| | % wt Lipoid/crown | 46.15 | 11.54 | 4.62 |
| | % mol. Lipoid/crown | 70.02 | 16.86 | 6.74 |
| | Cationic surfactant DOTAP | X | DOTAP | DOTAP |
| | % wt DOTAP/droplet | 0 | 26.47 | 26.47 |
| | % wt DOTAP/crown without PEG | 0 | 75 | 75 |
| | % wt DOTAP/crown | 0 | 34.61 | 34.61 |
| | % mol. DOTAP/crown | 0 | 54.28 | 54.24 |
| | Co-surfactant | Myrj S40 | Myrj S40 | Myrj S40 |
| | % wt co-surfactant droplet | 41.17 | 41.17 | 41.17 |
| | % wt (co-surfactant) crown | 53.85 | 53.85 | 53.85 |
| | % mol. (co-surfactant)/crown | 29.98 | 28.86 | 28.84 |
| | Fusogenic ipid DOPE | X | X | DOPE |
| | % wt DOPE/droplet | 0 | 0 | 5.29 |
| | % wt DOPE/crown without PEG | 0 | 0 | 15 |
| | % wt DOPE/crown | 0 | 0 | 6.92 |
| | % mol. DOPE/crown | 0 | 0 | 10.18 |
| CORE | Solubilizing Lipid | Suppocire NB | Suppocire NB | Suppocire NB |
| | % wt solubilizing lipid/core | 75 | 75 | 75 |
| | % wt solubilizing lipid/droplet | 17.65 | 17.65 | 17.65 |
| | Oil | Soya oil | Soya oil | Soya oil |
| | % wt oil/core | 25 | 25 | 25 |
| | % wt oil/droplet | 5.88 | 5.88 | 5.88 |
| | Formulation (number of repetitions) | 3 | 4 | 3 |
| RESULT | Hydrodynamic diameter (nm) - average | 124.9 | 49.1 | 44.48 |
| | ZP (mV)_in NaCl 0.15 mM | −26 | 25.38 | 30.87 |
| | Stability | ok | ok | Ok |
| | Complexation (%) | 0 | 100 | 100 |
| | Extinction efficiency (%) | 0 | 72.88 | 75.06 |

TABLE 2

| | | B1 (comp.) | B2 | B3 |
|---|---|---|---|---|
| CROWN | Amphiphilic lipid: Lipoid | S75-3 | S75 | S100-3 |
| | % wt Lipoid/droplet | 8.75 | 4.25 | 4.25 |
| | % wt Lipoid/crown without PEG | 100 | 50 | 50 |
| | % wt Lipoid/crown | 15.98 | 7.99 | 7.99 |

TABLE 2-continued

|  |  | B1 (comp.) | B2 | B3 |
|---|---|---|---|---|
|  | % mol. Lipoid/crown | 34.14 | 17.89 | 17.89 |
|  | Cationic surfactant DOTAP | X | DOTAP | DOTAP |
|  | % wt DOTAP/droplet | 0 | 4.25 | 425 |
|  | % wt DOTAP/crown without PEG | 0 | 50 | 50 |
|  | % wt DOTAP/crown | 0 | 7.99 | 7.99 |
|  | % mol. DOTAP/crown | 0 | 17.85 | 17.85 |
|  | Co-surfactant | Myrj S40 | Myrj S40 | Myrj S40 |
|  | % wt co-surfactant/droplet | 46 | 46 | 46 |
|  | % wt (co-surfactant)/crown | 84.02 | 84.02 | 84.02 |
|  | % mol. (co-surfactant)/crown | 65.86 | 64.27 | 64.27 |
|  | Fusogenic lipid DOPE | X | X | X |
|  | % wt DOPE/droplet | 0 | 0 | 0 |
|  | % wt DOPE/crown without PEG | 0 | 0 | 0 |
|  | % wt DOPE/crown | 0 | 0 | 0 |
|  | % mol. DOPE/crown | 0 | 0 | 0 |
| CORE | Solubilizing lipid | Suppocire NB | Suppocire NB | Suppocire NB |
|  | % wt solubilizing lipid/core | 75 | 75 | 75 |
|  | % wt solubilizing lipid/droplet | 33.94 | 33.94 | 33.94 |
|  | Oil | Soya oil | Soya oil | Soya oil |
|  | % wt oil/core | 25 | 25 | 25 |
|  | % wt oil/droplet | 11.31 | 11.31 | 11.31 |
|  | Formulation (number of repetitions) | 6 | 2 | 2 |
| RESULT | Hydrodynamic diameter (nm) - average | 59.51 | 42.11 | 61.43 |
|  | ZP (mV)_in NaCl 0.15 mM | −21.8 | 21.4 | 6.72 |
|  | Stability | ok | ok | ok |
|  | Complexation (%) | 0 | ND | ND |
|  | Extinction efficiency (%) | 0 | 0 | 0 |

TABLE 3

|  |  | B4 (comp.) | B5 | B6 |
|---|---|---|---|---|
| CROWN | Amphiphilic lipid: Lipoid | S75-3 | S75-3 | S75-3 |
|  | % wt Lipoid/droplet | 6.58 | 2.19 | 2.84 |
|  | % wt Lipoid/crown without PEG | 100 | 25 | 25 |
|  | % wt Lipoid/crown | 14.29 | 4 | 6.9 |
|  | % mol. Lipoid/crown | 31.24 | 8.39 | 12.39 |
|  | Cationic surfactant DOTAP | X | DOTAP | DOTAP |
|  | % wt DOTAP/droplet | 0 | 6.56 | 8.52 |
|  | % wt DOTAP/crown without PEG | 0 | 75 | 75 |
|  | % wt DOTAP/crown | 0 | 11.99 | 20.67 |
|  | % mol. DOTAP/crown | 0 | 26.99 | 39.87 |
|  | Co-surfactant | Myrj S40 | Myrj S40 | Myrj S40 |
|  | % wt co-surfactant/droplet | 39.48 | 46 | 29.87 |
|  | % wt (co-surfactant)/crown | 85.71 | 84.02 | 72.43 |
|  | % mol. (co-surfactant)/crown | 68.76 | 64.63 | 47.74 |
|  | Fusogenic lipid DOPE | X | X | X |
|  | % wt DOPE/droplet | 0 | 0 | 0 |
|  | % wt DOPE/crown without PEG | 0 | 0 | 0 |
|  | % wt DOPE/crown | 0 | 0 | 0 |
|  | % mol. DOPE/crown | 0 | 0 | 0 |
| CORE | Solubilizing lipid | Suppocire NB | Suppocire NB | Suppocire NB |
|  | % wt solubilizing lipid/core | 75 | 75 | 75 |
|  | % wt solubilizing lipid/droplet | 40.46 | 33.94 | 44.07 |
|  | Oil | Soya oil | Soya oil | Soya oil |
|  | % wt oil/core | 25 | 25 | 25 |
|  | % wt oil/droplet | 13.49 | 11.31 | 14.69 |
|  | Formulation (number of repetitions) | 3 | 4 | 6 |
| RESULT | Hydrodynamic diameter (nm) - average | 84.88 | 56.68 | 86.77 |
|  | ZP (mV)_in NaCl 0.15 mM | −18.89 | 26.51 | 36.38 |
|  | Stability | Ok | ok | ok |
|  | Complexation (%) | 0 | 100 | 100 |
|  | Extinction efficiency (%) | 0 | 0 | 42.81 |

TABLE 4

|  |  | B9 (Comp.) | B10 |
|---|---|---|---|
| CROWN | Amphiphilic lipid: Lipoid | S75-3 | S75-3 |
|  | % wt Lipoid/droplet | 0 | 1.71 |
|  | % wt Lipoid/crown without PEG | 0 | 15 |

TABLE 4-continued

|  |  | B9 (Comp.) | B10 |
|---|---|---|---|
| | % wt Lipoid/crown | 0 | 4.14 |
| | % mol. Lipoid/crown | 0 | 7.43 |
| | Cationic surfactant DOTAP | DOTAP | DOTAP |
| | % wt DOTAP/droplet | 8.25 | 8.25 |
| | % wt DOTAP/crown without PEG | 75 | 75 |
| | % wt DOTAP/crown | 20.67 | 20.67 |
| | % mol. DOTAP/crown | 39.87 | 39.87 |
| | Co-surfactant | Myrj S40 | Myrj S40 |
| | % wt co-surfactant/droplet | 29.87 | 29.87 |
| | % wt (co-surfactant)/crown | 72.43 | 72.43 |
| | % mol. (co-surfactant)/crown | 47.74 | 47.74 |
| | Fusogenic lipid DOPE | DOPE | DOPE |
| | % wt DOPE/droplet | 2.84 | 1.71 |
| | % wt DOPE/crown without PEG | 25 | 10 |
| | % wt DOPE/crown | 6.9 | 2.76 |
| | % mol. DOPE/crown | 10.18 | 4.99 |
| CORE | Solubilizing lipid | Suppocire NB | Suppocire NB |
| | % wt solubilizing lipid/core | 75 | 75 |
| | % wt solubilizing lipid/droplet | 44.07 | 44.07 |
| | Oil | Soya oil | Soya oil |
| | % wt oil/core | 25 | 25 |
| | % wt oil/droplet | 14.69 | 14.69 |
| | Formulation (number of repetitions) | 1 poor formulation | 5 |
| RESULT | Hydrodynamic diameter (nm) - average | ND | 88.64 |
| | ZP (mV)_in NaCl 0.15 mM | ND | 36.9 |
| | Stability | ND | Ok |
| | Complexation (%) | ND | 100 |
| | Extinction efficiency (%) | ND | 49.34 |

TABLE 5

|  |  | C1 (comp.) | C2 | C3 |
|---|---|---|---|---|
| CROWN | Amphiphilic lipid: Lipoid | S75-3 | S75-3 | S75-3 |
| | % wt Lipoid/droplet | 28.44 | 7.11 | 4.27 |
| | % wt Lipoid/crown without PEG | 100 | 25 | 15 |
| | % wt Lipoid/crown | 70.24 | 17.56 | 10.54 |
| | % mol. Lipoid/crown | 86.55 | 20.65 | 12.38 |
| | Cationic surfactant DOTAP | X | DOTAP | DOTAP |
| | % wt DOTAP/droplet | 0 | 21.33 | 21.33 |
| | % wt DOTAP/crown without PEG | 0 | 75 | 75 |
| | % wt DOTAP/crown | 0 | 52.68 | 52.68 |
| | % mol. DOTAP/crown | 0 | 66.51 | 66.47 |
| | Co-surfactant | Myrj S40 | Myrj S40 | Myrj S40 |
| | % wt co-surfactant/droplet | 12.05 | 12.05 | 12.05 |
| | % wt (co-surfactant)/crown | 29.76 | 29.76 | 29.76 |
| | % mol. (co-surfactant)/crown | 13.45 | 12.84 | 12.83 |
| | Fusogenic lipid DOPE | X | X | DOPE |
| | % wt DOPE/droplet | 0 | 0 | 2.84 |
| | % wt DOPE/crown without PEG | 0 | 0 | 10 |
| | % wt DOPE/crown | 0 | 0 | 7.02 |
| | % mol. DOPE/crown | 0 | 0 | 8.32 |
| CORE | Solubilizing lipid | Suppocire NB | Suppocire NB | Suppocire NB |
| | % wt solubilizing lipid/core | 75 | 75 | 75 |
| | % wt solubilizing lipid/droplet | 44.63 | 44.63 | 44.63 |
| | Oil | Soya oil | Soya oil | Soya oil |
| | % wt oil/core | 25 | 25 | 25 |
| | % wt oil/droplet | 14.88 | 14.88 | 14.88 |
| | Formulation (number of repetitions) | 4 | 4 | 3 |
| RESULT | Hydrodynamic diameter (nm) - average | 153.03 | 162.2 | 168.9 |
| | ZP (mV)_in NaCl 0.15 mM | −37.71 | 53.7 | 51.83 |
| | Stability | Ok | Ok | Ok |
| | Complexation (%) | 0 | 100 | 100 |
| | Extinction efficiency (%) | 0 | 80.51 | 81.72 |

In tables 1 to 5:

% wt corresponds to a mass percent.

% mol. Corresponds to a molar percentage.

ND (not determined) means that the experiment was not conducted.

The percentages "/droplet" represents percentages relatively to the (Lipoid/DOTAP/Myrj S40/optional DOPE/Suppocire NB/Soys oil) assembly.

The percentages "/crown" represent percentages relatively to the (Lipoid/DOTAP/Myrj S40/optional DOPE) assembly.

The percentages "/crown without PEG" represent percentages relatively to the (Lipoid/DOTAP/optional DOPE) assembly.

The percentages "/core" represent percentages relatively to the (Suppocire NB/Soya oil) assembly.

Lipoid S75-3 comprises 65-75% of phosphatidylcholine. The aliphatic chains of the phospholipids are in majority saturated (average composition: 12-16% of C16:0, 80-85% of C18:0, <5% of C18:1, <2% of C18:2).

Lipoid S75 comprises 65-75% of phosphatidylcholine. The aliphatic chains of the phospholipids are in majority unsaturated (average composition: 17-20% of C16:0, 2-5% of C18:0, 8-12% of 018:1, 58-65% of C18:2, 4-6% of C18:3).

Lipoid S100-3 comprises >94% of phosphatidylcholine. The aliphatic chains of the phospholipids are in majority saturated (average composition: 12-16% of C16:0, 85-88% of C18:0, <2% of C18:1, <1% of C18:2).

The formulations A1, B1, B4 and C1 are comparative examples since they do not comprise any cationic co-surfactant.

Their zeta potentials are negative.

Complexation of siRNA does not occur at the surface of the droplets, according to what was expected.

The formulation B9 is a comparative example since it does not comprise any amphiphilic lipid. The emulsion was not able to be prepared.

The following preparation method was followed:
(i) Preparation of the oily phase:

Soya oil, suppocire NC, amphiphilic lipid, DOTAP, optional DOPE, were weighed and then mixed with dichloromethane before being heated to 60° C. in order to obtain a homogenous viscous solution. The dichloromethane gives the possibility of promoting solubilization. The solvents are then evaporated in vacuo.

(ii) Preparation of the aqueous phase:

During the phase for evaporating ethanol, the aqueous phase was prepared. In an Eppendorf of 5 ml, the co-surfactant, glycerol and the aqueous solution of PBS (NaCl 154 mM, pH 7.4) were mixed and then dissolved in a bath at 75° C.

(iii) Mixing both phases:

The oily phase was at about 40° C. (in viscous form) and the aqueous phase at about 70° C. (upon leaving the bath). The aqueous phase was poured into the oily phase.

(iv) Emulsification:

The flask containing both phases was attached in the sonication enclosure a sonicator AV505® (Sonics, Newton, USA). The procedure consisted in producing sonication cycles (10 seconds of activity every 30 seconds) at a power of 100 W over a period of 40 minutes.

(v) Purification:

The thereby produced droplets were then purified by dialysis (cut off threshold: 12 kDa, against NaCl 154 mM, overnight) in order to remove the lipid components not integrated to the LNPs. Finally, the formulation was sterilised by filtration on a cellulose membrane.

Size of the Droplets of the Formulations and Zeta Potential

Influence of the Composition of the Formulation

The results of table 1 to 5 show that a decrease in the proportion of co-surfactant (Myrj S40) leads to an increase in the diameter of the droplets.

Time Dependent Change

The time dependent change in the size of the droplets (Table 6) and of the zeta potential (table 7) of the formulations were measured at 40° C. (accelerated stability). The formulations were kept at 40° C. between two measurements.

TABLE 6

Time dependent change of the size of the droplets and of the polydispersity index (PDI) as measured by quasi-elastic scattering of light versus time

| Days | B1 | B4 | B5 | B6 | B10 | C1 | C2 |
|---|---|---|---|---|---|---|---|
| 0 | 58.27 | 98.87 | 60.03 | 87.93 | 91.53 | 157.43 | 171.4 |
| 7 | 60.52 | 97.12 | 58.96 | 87.1 | 90.51 | 156.17 | 172.63 |
| 14 | 62.59 | 98.36 | 58.28 | 86.25 | 89.87 | 156.46 | 170.15 |
| 21 | 59.41 | 97.81 | 59.23 | 85.78 | 90.3 | 153.03 | 162.2 |
| 28 | 61 | 97.15 | 60.36 | 87.61 | 90.96 | 153.9 | 161.47 |

TABLE 7

Time dependent change of the zeta potential of the formulations versus time.

| Days | B1 | B4 | B5 | B6 | B10 | C1 | C2 |
|---|---|---|---|---|---|---|---|
| 0 | −21.3 | −21.16 | 24.03 | 34.13 | 34.97 | −40.27 | 57.33 |
| 7 | −25.6 | −21.17 | 28.23 | 31.77 | 34.73 | −43.13 | 56.77 |
| 14 | −24.73 | −21.03 | 29.45 | 28.4 | 33.47 | −42.33 | 55.33 |
| 21 | −21.8 | −20.47 | 28.63 | 34.3 | 33.07 | −38.1 | 53.9 |
| 28 | −18.93 | −19.83 | 27.5 | 33 | 31.23 | −39.03 | 51.6 |

It was observed that the size of the droplets and the zeta potential of formulations according to the invention kept at 40° C. for 300 days do not change.

These results show that the formulations according to the invention are stable over time.

1.2. Complexation with siRNAs

The following general procedure was followed:

The complexation consists in a simple mixture of the formulations prepared above and of an siRNA solution, the whole in a buffer. The selection of the buffer depends on the envisioned application: for a study in vitro, the optimized culture medium for the transfection steps, OptiMEM, was used. For a complexation study, buffer Hepes 5 mM was used.

An amount of 0.5 µg of siRNA (GFP-22 siRNA rhodamine (catalogue no. 1022176) (Qiagen) or siGFP (Sigma)) was used (25 µg/mL in 20 µL).

The mixture was stirred for 30 minutes at 600 rpm, this at room temperature (about 25° C.).

The complexation was viewed through two tools:

Agarose gel electrophoresis which allows observation of the migration of the siRNAs. If there is good complexation, then the droplets comprising the complexed siRNAs will be heavier than the free siRNAs and will be viewed in the wells. If the complexation is less significant, free siRNAs migrate to another position.

In DLS, by observing the impact of the complexation on the hydrodynamic diameter, the more efficient is complexation, the more the profile is oriented towards a single mode distribution.

The amount of formulation required for having a quantitative complexation yield of the siRNAs was optimized.

In practice, the negative charges brought by the siRNAs are compensated by the positive charges of the formulation (i.e., the positive charges of the cationic surfactant DOTAP).

Figure 2:
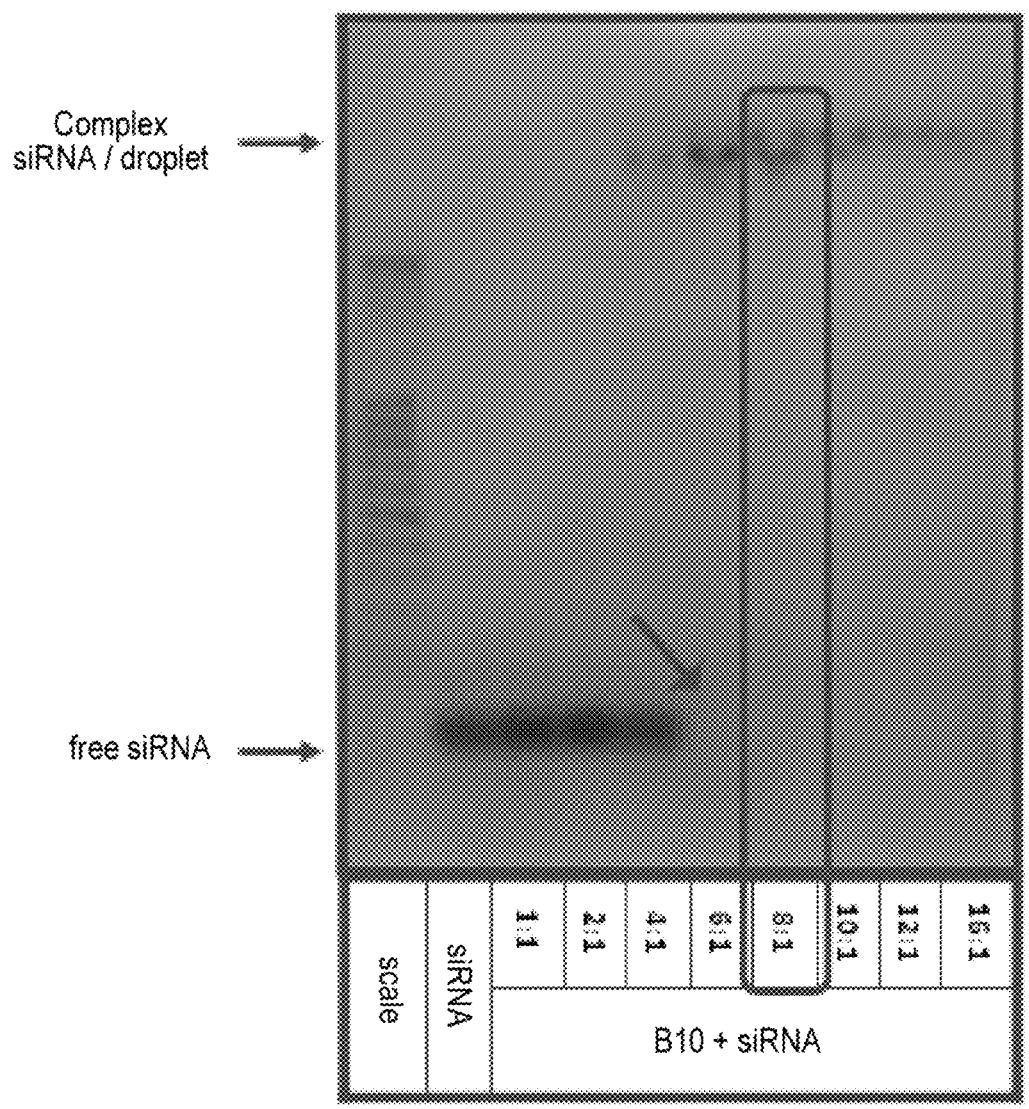
Figure 3:
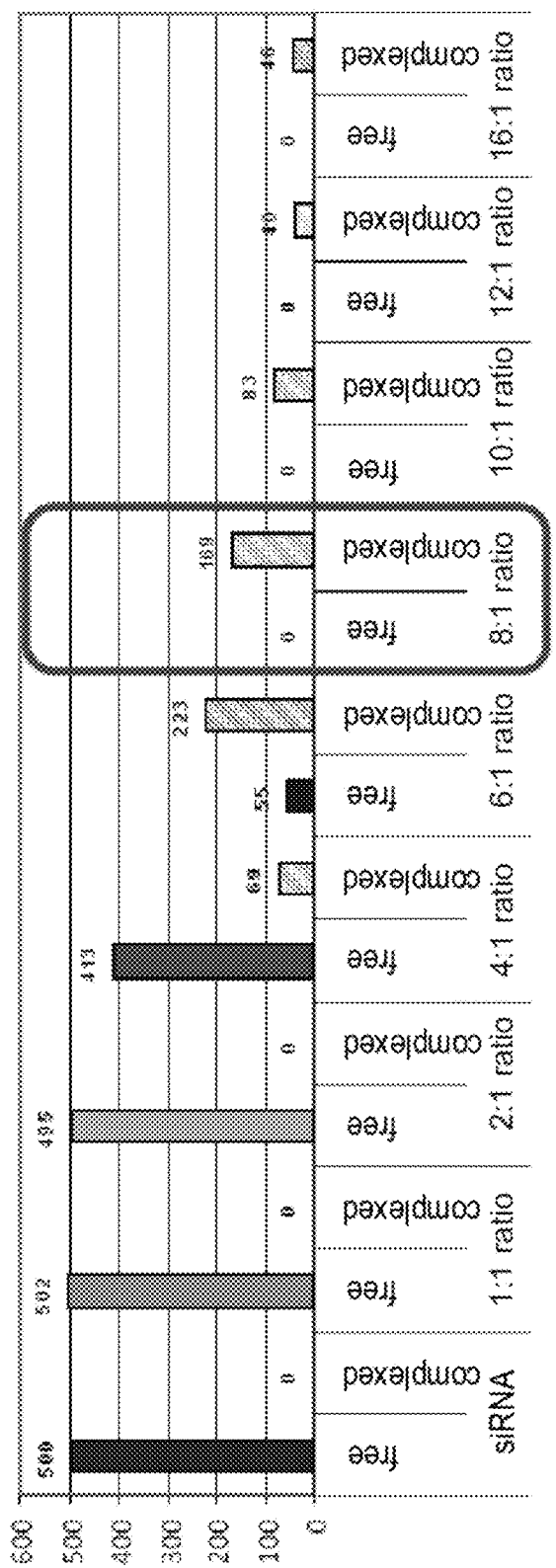

Typically, when the sole cationic surfactant of the formulation is DOTAP (which only comprises a single positive charge), a quantitative complexation yield is obtained when the ratio of the amount of positive charges due to the cationic surfactant in the «premix» formulation over the amount of negative charge brought by the siRNAs is greater than 8/1, as illustrated in FIGS. 2 and 3.

FIG. 2 illustrates an electrophoresis gel revealed under UVs produced after complexation of siRNA with the formulation B10 with concentrations specified in table 8, by mixing an siRNA solution and the formulation in a Hepes buffer 5 mM. After deposition on 1.5% agarose gel, 2 µL of charged buffer were added to the tests. After 1 h 30 min of electrophoresis at 100 V, the gel was immersed in GelRed 3×. Finally, development with UVs was carried out.

TABLE 8

| Ratio of the amount of positive charges due to the cationic surfactant in the "premix" formulation over the amount of negative charge provided by the siRNAs | 1/1 | 2/1 | 4/1 | 6/1 | 8/1 | 10/1 | 12/1 | 16/1 |
|---|---|---|---|---|---|---|---|---|
| siRNA concentration (µg/mL) | | | | | 25 | | | |
| DOTAP concentration (µg/mL) | 0 | 25 | 50 | 100 | 150 | 200 | 250 | 300 | 400 |

FIG. 3 gives the results obtained by processing the data from the electrophoresis on the software package ImageJ of the same experiments.

FIGS. 2 and 3 show that for a ratio of the amount of positive charges due to the cationic surfactant in the "premix" formulation over the amount of negative charge provided by the siRNAs, greater than 8/1, there is no longer any free siRNA in the medium and the siRNA has been completely complexed.

Figure 4:
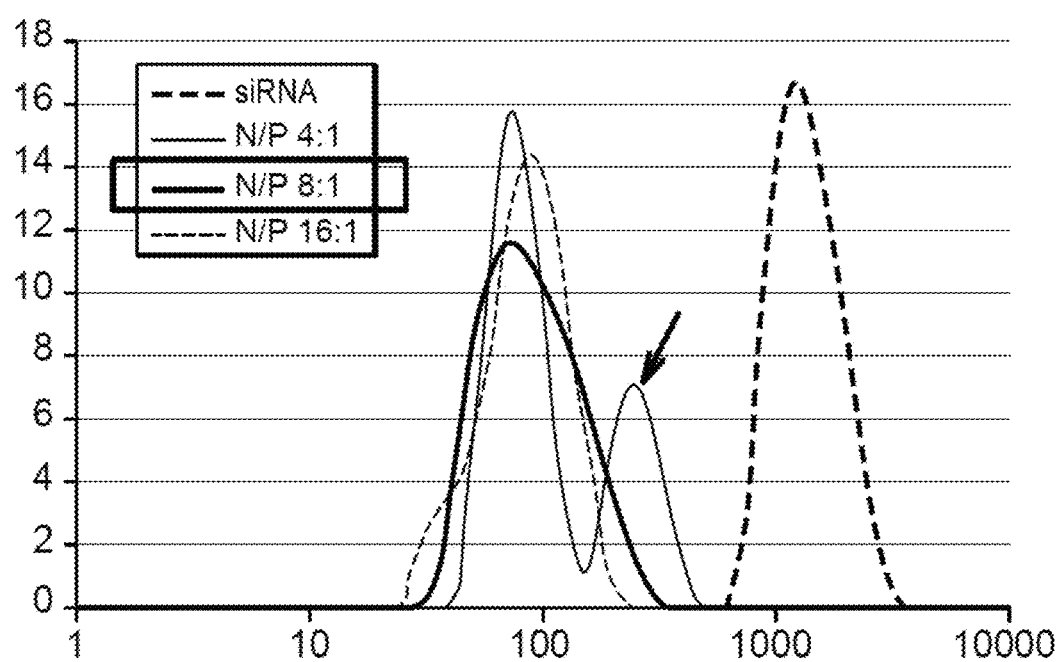

FIG. 4 illustrates the intensity obtained on a ZetaSizer Malvern apparatus according to the hydrodynamic diameter in nm for free siRNA (comparison) and for three formulations according to the invention obtained by complexation with a ratio of the amount of positive charges due to the cationic surfactant in the "premix" formulation over the amount of negative charge brought by the siRNAs of 4/1, 8/1 or 16/1.

The diameter is larger for free siRNA (comparison).

With a ratio of the amount of positive charges due to the cationic surfactant in the "premix" formulation over the amount of negative charge brought by the siRNAs, of 4/1, 2 populations are observed: an siRNA/droplet complex around 100 nm and a population of a larger size representing the siRNAs in free form (arrow).

With the ratios of the amount of positive charges due to the cationic surfactant in the "premix" formulation over the amount of negative charge provided by the siRNAs, of 8/1 and 16/1, only a single population representing the siRNA/droplet complex was observed.

These results also show that quantitative complexation (100%) of the siRNAs on the droplets is allowed.

The complexation step was carried out with diverse formulations.

As a comparison, a complexation test was conducted with a formulation free of cationic surfactant: the formulation B1 described above. As expected, complexation of the siRNA did not occur and the siRNA remained in free form.

Figure 5:
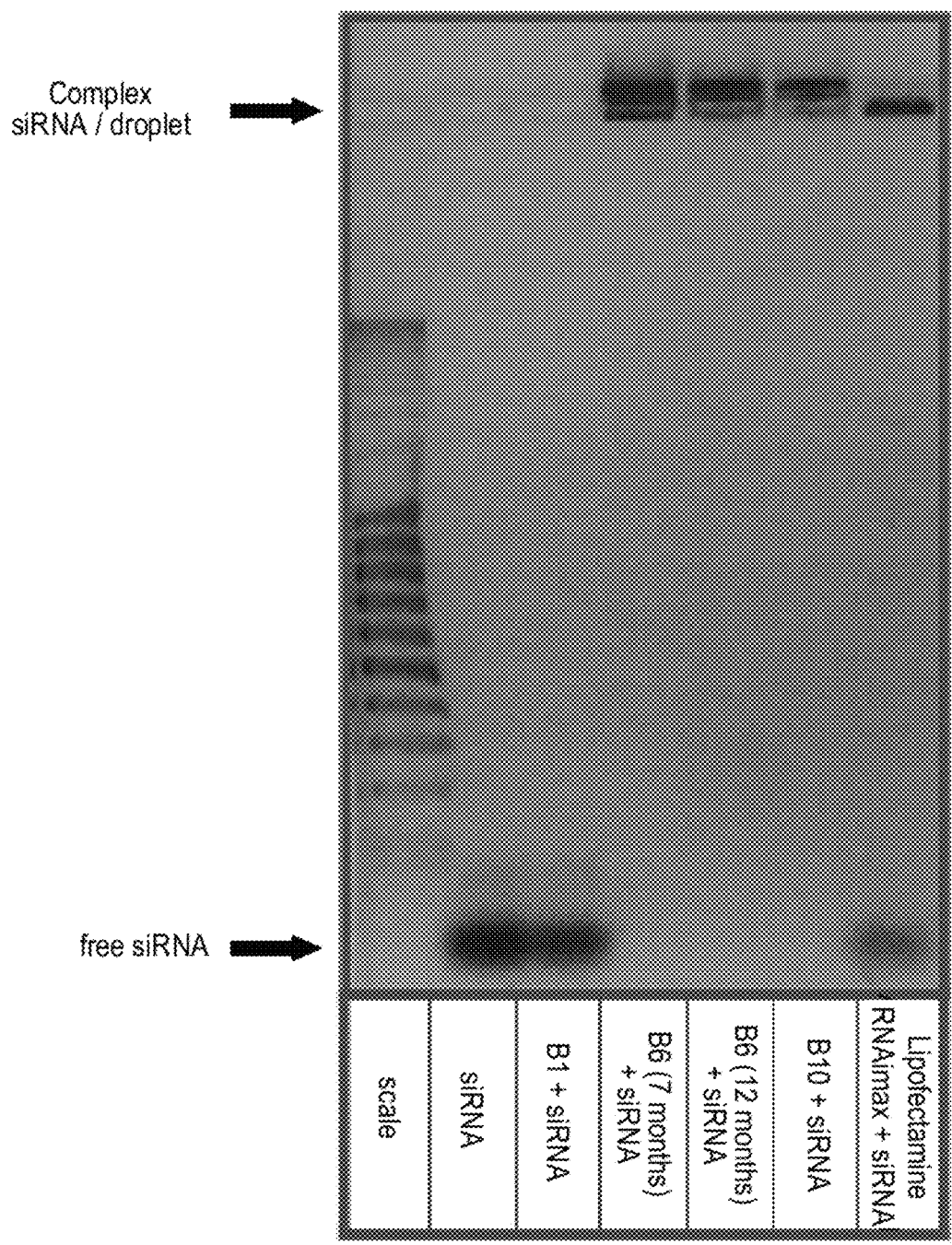

FIG. 5 illustrates an electrophoresis gel revealed with UV with, from left to right:
the scale,
the free siRNA (control)
and then migrations obtained by complexation of siRNA:
  with the formulation B1 (comparative example) (no complexation, the siRNAs are free),
  with the formulation B6 (a premix formulated 6 months before) with a ratio of the amount of positive charges due to the cationic surfactant in the "premix" formulation over the amount of negative charge brought by the siRNAs, of 8/1 (quantitative complexation),
  with the formulation B6 (a premix formulated 12 months before) with a ratio of the amount of positive charges due to the cationic surfactant in the "premix" formulation over the amount of negative charge provided by the siRNAs, of 8/1, the formulation having been kept for 7 months at room temperature before complexation (quantitative complexation),
  with the formulation B10 with a ratio of the amount of positive charges due to the cationic surfactant in the "premix" formulation over the amount of negative charge brought by the siRNAs, of 8/1 (quantitative complexation),
  with lipofectamine (comparative example) (incomplete complexation).

The complexation of siRNA is quantitative when the formulations B6 or B10 were used. The storage of the formulation at room temperature before its complexation with siRNA has no influence on the complexation yield, which remains quantitative, which shows the stability of the formulations used.

The yield is quantitative regardless of whether the formulation used comprises or not DOPE.

With the commercial transfection agent Lipofectamine RNAimax, more than 60% of the siRNAs were found in free form. This implies that the formulations of nanoemulsions used in the invention provide a better complexation yield than Lipofectamine.

Figure 6:
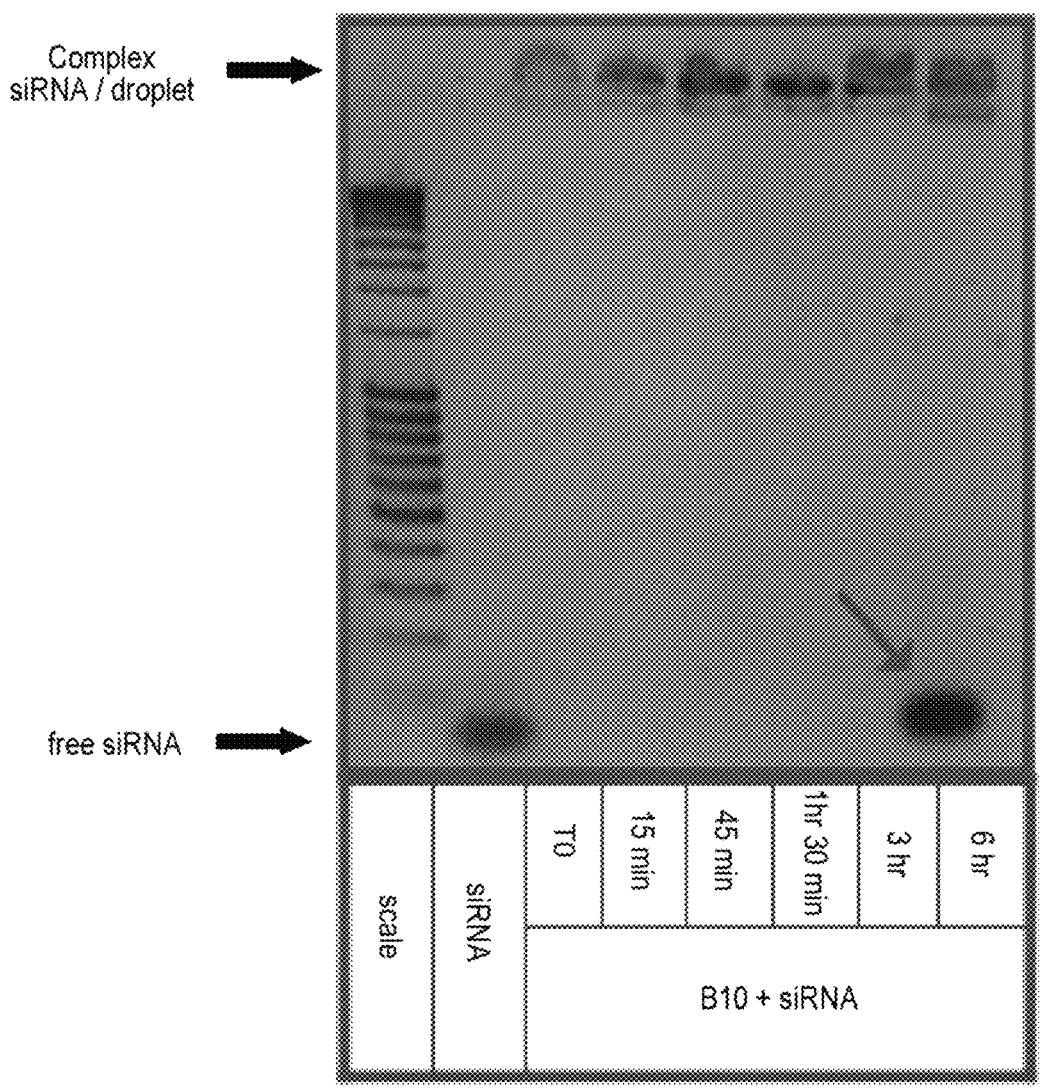

Finally, siRNA sorting-out kinetics of the siRNA/formulation B10 complex prepared above were effected in order to observe the time dependent change of the complexation and is illustrated in FIG. 6. Up to 3 hours after complexation, the siRNAs were not found in free form. At 6 hours, the siRNAs begin to be sorted out. The complex is therefore stable for at least three hours.

1.3. Transfection in vitro

Preliminary transfection tests of the nanoparticles defined in example 1.1. and complexed according to Example 1.2. with an siRNA specifically inhibiting a sequence of messenger RNA of GFP (GFP-22 siRNA rhodamine (catalogue no. 1022176) (Qiagen)) were conducted on different cell lines over expressing the Green Fluorescent Protein (GFP).

The transfection was carried out with a final siRNA concentration of 100 nM.

Thus, cells expressing GFP were sown in 12-well plates (25,000 cells/well) and then treated with siRNA/Formulations (B1, B6, B6 7 months after its preparation or B10) complexes obtained above. The cells are then incubated for 72 hours at 37° C., and then recovered for analysing the fluorescence intensity with the flow cytometer in order to determine the efficiency of the formulation as a transfection agent. The active delivery of siRNA specifically inhibiting the expression of the GFP protein induces a decrease in the fluorescence brought by this protein.

The commercial transfection agent, Lipofectamine RNAimax was used as a comparison.

Figure 7:
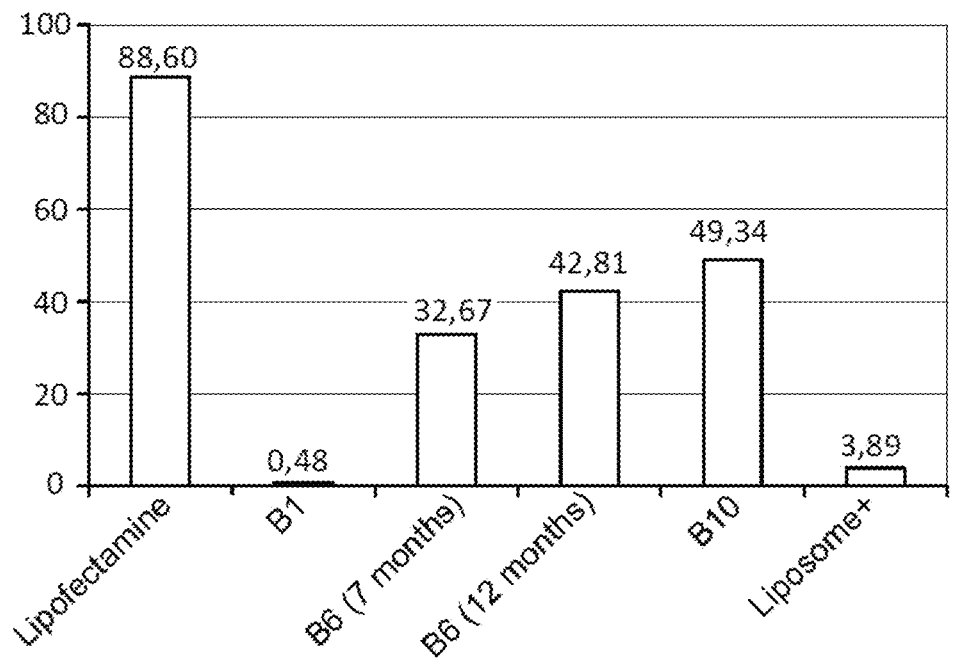

FIG. 7 illustrates the decrease in the fluorescence intensity FITC in % upon transfecting cell lines with:
- Lipofectamine RNAimax,
- siRNA/formulation B1 complex,
- with the siRNA/formulation B6 complex, the formulation having been kept for 7 months at room temperature before complexation,
- with the siRNA/formulation B6 complex, the formulation having been kept for 12 months at room temperature before complexation,
- with the siRNA/formulation B10 complex,
- with an siRNA/formulation of cationic liposomes comprising DOTAP (58% wt), DOPE (18% wt), cholesterol (2% wt) and DSPE-PEG3000 (22% wt)) (comparative) complex.

Thus, a decrease of the fluorescence by 33 to 50% is observed with the formulations according to the invention which were tested. The formulations according to the invention therefore allow active delivery of siRNA inducing relative extinction of the expression of the gene of GFP.

Further, by incorporating DOPE into the formulations, a more substantial extinction of fluorescence is visible, DOPE promoting endosomal escape.

No decrease in the fluorescence was observed with the siRNA/formulation of cationic liposomes complex, which may for example be explained by poor stability of the liposomes in the culture medium, a poor complexation yield and/or a poor retention of the siRNAs by the liposomes after complexation.

Figure 8:
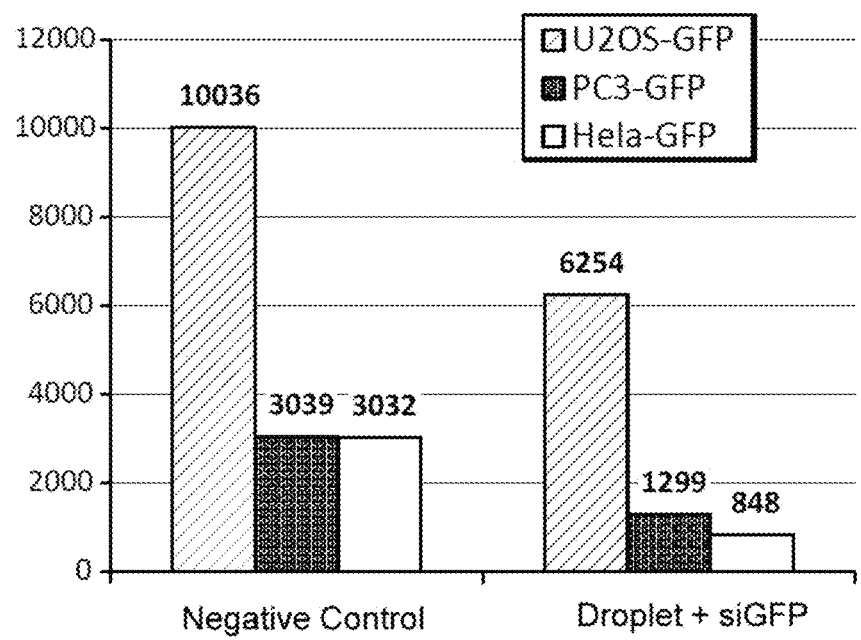

Finally, such results on the active delivery of siRNA mediated by the formulations according to the invention were reproduced on 3 cell lines expressing GFP: U2OS, PC3 and Hela, as illustrated in FIG. 8.

1.4. Complexation with Single DNA Tags

Complexation consists in a simple mixing of the formulations prepared above and of an siRNA solution, the whole in a buffer. The selection of the buffer depends on the envisioned application: for a study in vitro, the optimized culture medium for transfection steps, OptiMEM, was used. For a complexation study, Hepes buffer 5 mM was used. The mixture is stirred for at least 30 minutes at 600 rpm, this at room temperature (about 25° C.).

1.5. Encapsulation of the Fluorophore

The encapsulation of the fluorophore is achieved according to the method defined in application WO2008104717. More specifically, the fluorescent nanoparticles are obtained by sonication of the oily phase in the aqueous phase. The oily phase comprises a mixture of soya oil and of Suppocire® NC as well as lecithin and fluorophores (for solubility reasons). The aqueous phase as for it comprises the pegylated surfactant, the aqueous solution (NaCl or PBS) and optionally glycerol in order to increase the viscosity of the mixture. The fluorescent nanoparticles are produced by batches of 2 or 5 mL. Briefly, the oily phase is prepared by mixing the soya oil, Suppocire® NC and lecithin (dispersed phase+lecithin). An organic solvent (dichloromethane) is added in order to facilitate dissolution of lecithin. Once all the compounds are dissolved, the solvent is evaporated in vacuo at a temperature above the boiling point of the wax. The fluorescent molecules are then added into the oily phase. In order to facilitate their dispersion, the fluorophores are dissolved beforehand in an organic solvent (ethanol). The solution is homogenized and the organic solvent is removed by evaporation in vacuo. The aqueous phase is prepared by hot mixing of glycerol, of the pegylated surfactant and of the aqueous phase. Both phases maintained beforehand at about 50° C. are mixed and then homogenized with ultrasound, so as to form nanoparticles trapping in their cores the lipophilic fluorophores. The solutions of fluorescent nanoparticles obtained are then purified by dialysis so as to remove the molecules which possibly have not been encapsulated.

1.6. Preparation of the Library of Nanoparticles

The preparation of 1000 fluorescent nanoparticles is carried out by using siRNAs from the collection of 1292 siRNAs from Qiagen targeting 646 kinases (Human Kinase siRNA set V1.0; Ref. 1027091), or the collection of 2375 siRNAs from Qiagen targeting 1183 genes involved in cancers (Human Cancer siRNA set V2.0), or the collection of 278 siRNAs targeting 139 genes involved in cancers (Human Cancer siRNA set V1.0; Ref. 1022171), or the collection of 91,800 siRNAs from Qiagen targeting 22,950 human genes (Human Genome Wide siRNA set), or by using LNAs from the collection of 982 LNAs from Exiqon targeting all the known human miRNAs (miRCURY LNA Human microRNA Inhibitor Library; Ref. 190102-2).

The single DNA tag contains two sequences of 50 bp in 5' and in 3' allowing amplification of the tag flanking a single sequence of 10 bp containing synthetic bases. Each siRNA or each LNA of the collections is associated in silico with a single sequence of 10 bp.

Example 2

2D and 3D Cultivation of Prostate Cells

The following prostate cells are used:
- PTN1 and RWPE1 cells, which are immortalized normal epithelial cells of the prostate,
- the cells WPE1-NA22, WPE1-NB14, WPE1-NB11 and WPE1-NB26, which are derived from RWPE1 cells and which mimic different tumorigenesis stages after exposure to N-methyl-N-nitrosourea,
- the cell line 22Rv1, which is a line of human prostate carcinoma epithelial cells responding to a deficiency of androgens,
- the cell lines VcaP and LNCaP, which are metastatic prostate cancer cell lines in vitro and in vivo sensitive to androgens,
- the cell lines PC3 and DU145, which are metastatic prostate cancer cell lines which no longer respond to androgen deficiency,
- primary prostate cells from healthy subjects.

The 3D structure production in the form of acini from these prostate cells is also achieved.

The transfection efficiency and the toxicity of the nanoparticles comprising a fluorophore, an siRNA and a single DNA tag are evaluated on each of these prostate cell cultures.

Example 3

High Throughput Phenotype Analysis by Flow Cytometry

The cells are screened according to two different phenotypes: cell proliferation, cell death. The proliferation is evaluated by marking with propidium iodide, EdU, or Hoechst 33342. Cell death is evaluated by marking with Annexine V-FITC or by so called TUNEL ("Terminal deoxynucleotidyl transferase dUTP Nick End Labelling") marking or by the analysis of activation of caspases. For each of these phenotypes, the optimal conditions for marking and selecting the cells are evaluated, in order to select suitable positive and negative controls.

Once the conditions are determined for marking and selecting the cells according to their phenotype, primary screenings on about 10 prostate cell lines having different types of response to hormonal treatment or on prostate primary cells are carried out.

Example 4

Deconvolution of the Single DNA Tag, Analysis of the Data and Validation

A small aliquot of cells selected after flow cytometry is used for identifying the single DNA tag. The DNA is extracted from fluorescent cells, subject to PCR with universal primers, and sequenced with a second generation sequencer (Illumina or Roche 454 or ABI solid). The identification of the sequence of 10 bp of the single DNA tag is then correlated with the siRNA or the LNA which has been associated with it in silico. A list of genes for which inhibition by siRNA or LNA induces the phenotype of interest is then established. The screening method also allows the establishment of sets of functional genomic data for each of the cell lines tested according to their sensitivity to hormonal therapies, lists of genes coding for proteins or miRNAs which are potential markers of sensitivity to hormones.

A validation in vitro on the remaining cells of the occurrence of the phenotype and of the inhibition of the gene is achieved by quantitative real time PCR and by Western-blot.

Example 5

Validations in vivo and Clinical Validations

A validation strategy in two phases is achieved:
for validation in vivo, control human prostate cancer cells and prostate cancer cells transfected with the nanoparticles according to the invention (e.g. containing siRNAs or LNAs) are implanted in "nude" athymic cells. The volume of tumours is monitored and after euthanasia, the tumours are excised and fixed for immunohistological analysis of the proliferation or apoptosis in cells transformed with the nanoparticles according to the invention.

for clinical validation, commercial microchips of prostate tissues containing several hundred prostate cancer tissues of different grades are used.

This allows validation of biomarkers for prostate cancer, new therapeutic targets and siRNA as new therapeutic agents.

Example 6

Co-delivery of siRNA of Interest and of a DNA Tag (Bar Code) by Fluorescent Nanoparticles, Sorting of the Cells Having Incorporated the Nanoparticles According to a Phenotype of Interest and a Posteriori Identification of the Bar Code of the DNA Tag by Extracting DNA and Specific Amplification from the Sorted Cells 6.1. Complexation Between Different Nucleic Acids, Tag DNA and siRNA, with a Formulation of Fluorescent Nanoparticles In this example, co-transfection of the target cells is carried out with an siRNA of interest and a specific DNA tag of the siRNA by resorting to dispersion of fluorescent nanoparticles.

Figure 9:
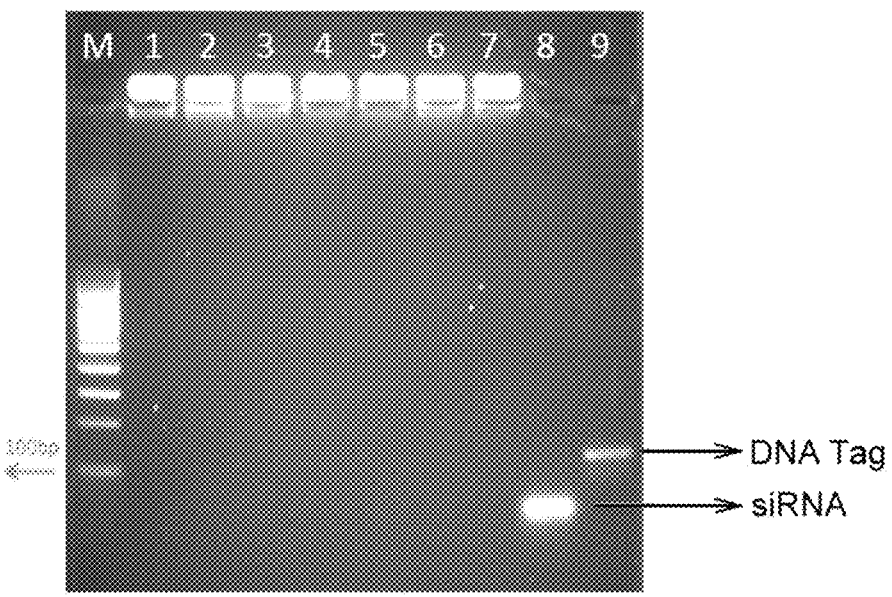

Gel Delay Experiment (FIG. 9):

The formulations of lipid nanoparticles used in this example were achieved according to the same manufacturing method as the one described in Example 1 and corresponds to the formulation A3. The general complexation procedure is the same as the one followed for example 1. Briefly, complexation consists in simply mixing a formulation A3 comprising a lipophilic fluorophore encapsulated in the core (DiD, Invitrogen, Ref. D7757) and of a siRNA and DNA tag solution with nanoparticles, the whole in a buffer. In this study, the buffer used is HEPES (5 mM, pH 7.2). For the well 1, the nanoparticles A3 were complexed with a solution containing 11 ng of siRNA (siAllStar Negative Control siRNA, Qiagen, Ref. 1027280) and 20 ng of DNA tag (Eurogentec). For the following wells (wells numbered from 2 to 7), this siRNA/DNA tag solution was diluted by a factor two before complexation with the nanoparticles, according to the cascade dilution technique. The N/P ratios used here (N=positive charge brought by the ammonium group of the nitrogen of the cationic lipids making up the crown of the lipid particle; P=negative charge brought by the phosphate group of the nucleic acids) are 12/1, 24/1, 48/1, 96/1, 192/1, 384/1, 768/1 for the wells 1 to 7 respectively. The mixture was stirred for 30 minutes at 600 rpm at room temperature (about 25° C.). An electrophoresis on agarose gel (gel with 1.5% of agarose with Agarose ultrapure 1000, Invitrogen, Ref. 16550100; buffer TBE 10X, Ref. 15581044; ultrapure water, Ref. 10977035) gives the possibility of demonstrating that both nucleic acids are actually complexed at the fluorescent lipid droplet, as illustrated in FIG. 9. Indeed, if the nanoparticles/siRNA/DNA tag complexes are stable, all the nucleic acids (siRNA and DNA tag) are retained in the wells (wells 1 to 7) and cannot migrate within the gel. Conversely, a free siRNA (not complexed with the nanoparticles) will be visible in the form of a band migrating towards 21 bp (well 8). Also, a free DNA tag (non-complexed with the nanoparticles) will migrate in the form of a visible band towards 129 bp (well 9). This experiment shows the efficiency of the lipid nanoparticles, of the type Lipidot® of formulation A3, to be simultaneously and in a stable way for complexing the siRNAs and the DNA tags.

6.2. Co-transfection of Two Nucleic Acids, siRNA and DNA Tag, by Fluorescent Nanoparticles A Transfection Experiment in vitro of HeLa Over Expressing GFP with Formulation A3/DNA Tag/siRNA Complexes:

Simultaneous delivery, in target cells in vitro, of the different molecules transported by the lipid nanoparticle (formulation A3) containing a fluorophore was evaluated.

Figure 10:
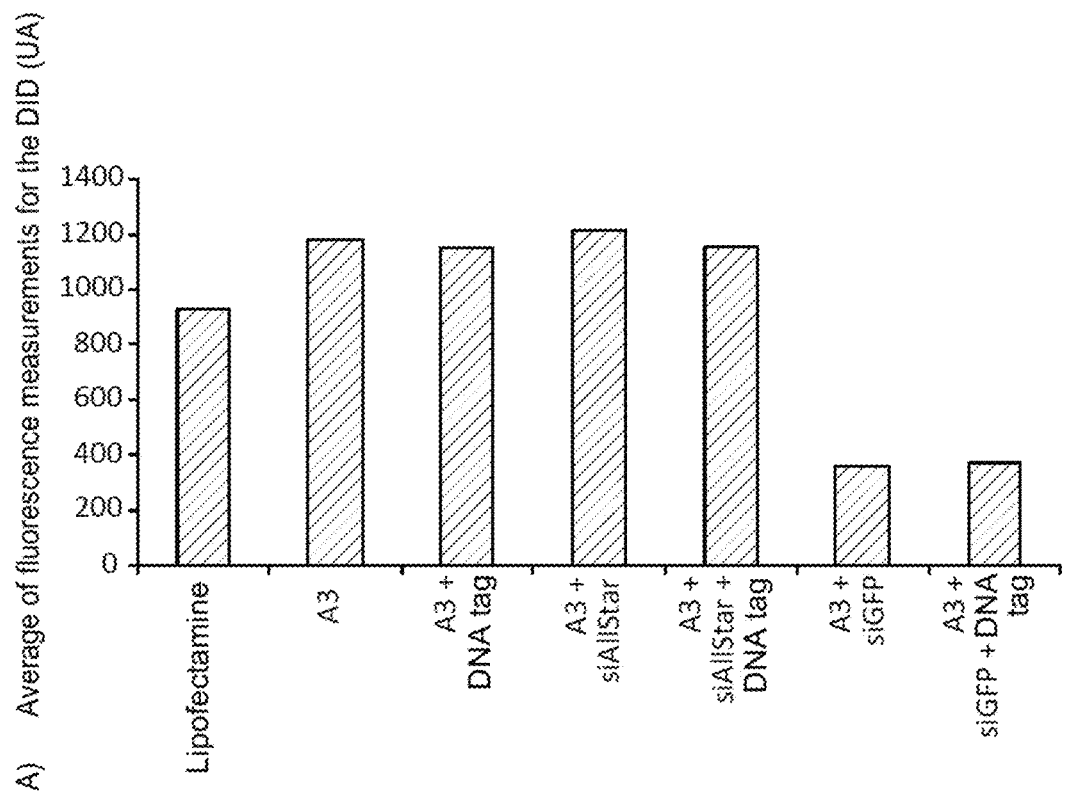
FIG. 10 illustrates the quantification of the averages of fluorescences for GFP after FACS analysis of the HeLa cells and incubated for 72 h with nanoparticles A3/DNA tag/siGFP complexes.
Figure 11:
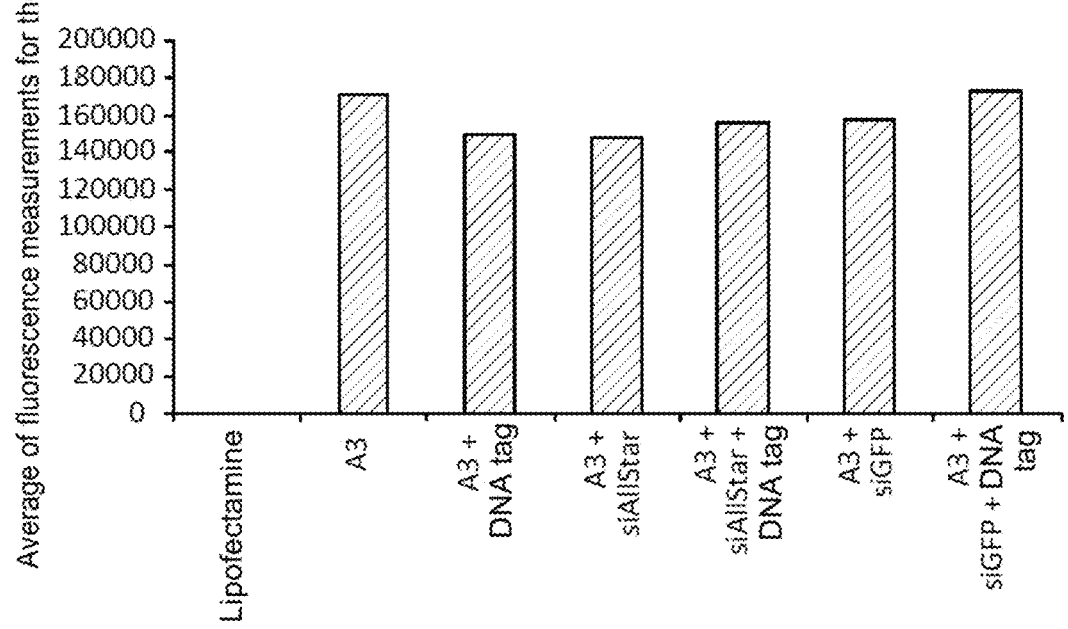
FIG. 11 illustrates the quantification of averages of fluorescences for the encapsulated DID fluorophore after FACS analysis of the HeLa cells and incubated for 72 h with nanoparticles A3/DNA tag/siGFP complexes.

To do this, a study was conducted on HeLa cells, i.e., cells stemming from uterine cervix cancer (ATCC, Ref. HeLa-CCL2), which were modified in order to over express the GFP protein. Active delivery of siRNA is validated by extinction of the GFP protein (decrease in the FITC signal) by specific screening of its mRNA by an siGFP. In parallel, the observation of the interaction of the fluorescent nanoparticles with the cell is made possible by studying the time dependent change of the fluorescent signal brought by the encapsulated fluorophore, DID (followed by the APC signal). This first step shows a very strong decrease in the FITC signal and therefore of the expression of GFP in cells treated with the nanoparticle A3/DNA tag/siGFP complex as well as an increase in the APC signal indicating the interaction of the fluorescent nanoparticles (bearing the fluorophore DID) with the cells (FIGS. 10 and 11).

These results show that the presence of tag DNA does not perturb the delivery of siRNA in the cells and that the functionality of the latter is preserved, i.e., the interaction with the mRNA coding for GFP and inhibition of the expression of this protein by an RNA interfering mechanism. The efficiency of extinction of FITC fluorescence corresponding to the expression of GFP is of the order of 70% in these experiments following incubation of the cells with the fluorescent nanoparticle A3/DNA tag/siRNA targeted against mRNA of GFP complexes (FIG. 10).

Figure 12:
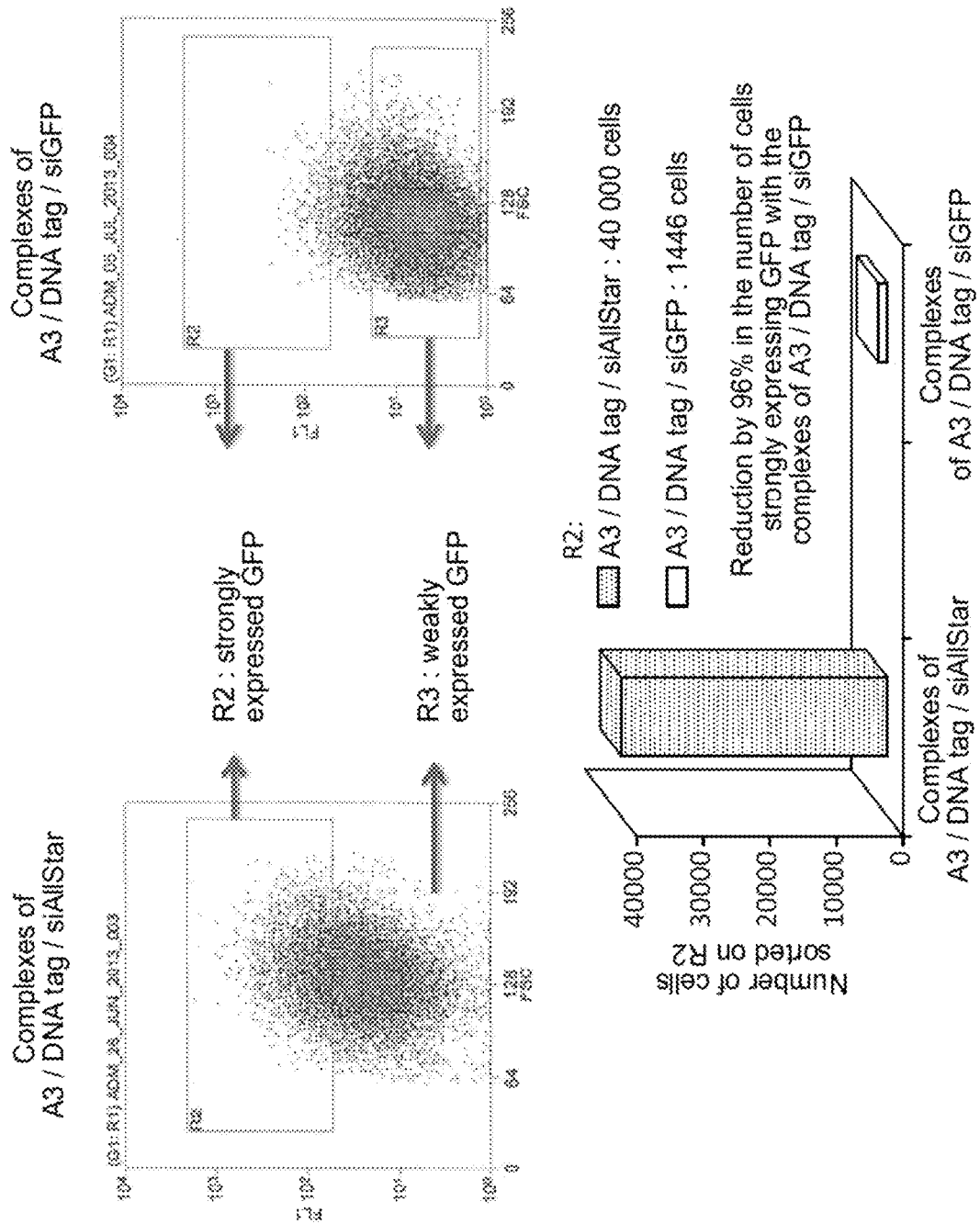
FIG. 12 illustrates the FACS analysis of the FITC signal corresponding to expression of GFP by the HeLa cells. The sorting of these cells was accomplished according to their criterion of expression of GFP and allows identification of two populations: a population which strongly expresses GFP and a population which weakly expresses GFP.
Figure 13:
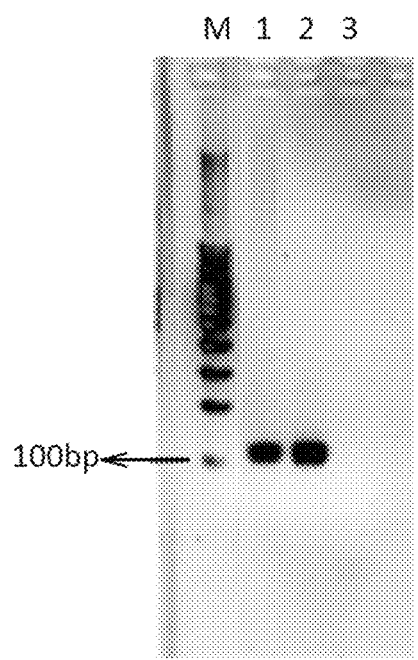
FIG. 13 illustrates an electrophoresis gel of the DNA tags after extraction and amplification with PCR on HeLa cells sorted beforehand.

Identification of the DNA Tag in the Sorted Cells on the Basis of GFP Extinction After Transfection by A3/DNA Tag/siRNA Complexes:

In this experiment, the cell populations strongly or weakly expressed in GFP were sorted by flow cytometry (Cytomation, MoFlo). In practice, 200,000 HeLa-GFP cells were sown in wells of 6-well plates. After 24 hours of cultivation, these cells were transfected with fluorescent nanoparticles A3/DNA tag/siAllStar complexes or fluorescent nanoparticles A3/DNA tag/siGFP complexes. Seventy two hours after transfection, the cells are detached from the wells by adding trypsin. The cells contained in three wells for a same transfection condition are added and sorted into two distinct populations, according to their strong or weak expression level of GFP (FIG. 12). The DNA content of the thereby recovered cells is extracted via the QiaAmp DNA mini kit (Qiagen, Ref. 51304) and then a PCR is carried out by using the specific primers of the DNA tag. The primers used for this amplification are the pGEX 3' and 5' primers (Eurogentec, Ref. UN-PR130-005 and UN-PR135-005). The PCR is carried out with 35 amplification cycles (Qiagen, HotStarTaq Master Mix, Ref. 203443). The thereby amplified nucleic acids are then deposited in the wells of a 2% agarose gel prepared beforehand. In FIG. 13, we may observe that the cells transfected with the fluorescent nanoparticles A3/DNA tag/siGFP complexes have a very strong decrease in the expression of GFP, and also bear the DNA tag which is detected by PCR. This result shows the capability of the fluorescent nanoparticles of formulation A3 of simultaneously delivering within the cells, a DNA tag and a functional siRNA.

These results demonstrate:

that the nanoparticles according to the invention allow simultaneous delivery in target cells of two nucleic acids (siRNA and DNA tag), the cells transfected by siRNA being therefore fluorescent.

the feasibility of the sorting of the cells having incorporated the fluorescent nanoparticles and having a phenotype of interest, the feasibility of a posteriori identification of the siRNA of interest by analysing the bar code of the DNA tag specifically associated with this siRNA, after extraction of cell DNA and amplification of the tag DNA.

The invention claimed is:

1. A method for screening a molecule of interest comprising:
   (a) transfecting cells with a library of synthetic nanoparticles comprising a plurality of candidate molecules, a tracer, and a plurality of different unique DNA tags that are specific to the plurality of candidate molecules, wherein each synthetic nanoparticle of the library of synthetic nanoparticles is a droplet of an oil-in-water emulsion, each synthetic nanoparticle of the library of synthetic nanoparticles comprising:
      (1) the tracer, wherein tracer is selected from the group consisting of a magnetic tracer, a radioactive tracer, and a fluoropolymer,
      (2) one of the candidate molecules of the plurality of candidate molecules, said one of the candidate molecules being localized at the surface of each nanoparticle,
      (3) a single unique DNA tag of the plurality of different single unique DNA tags, said single unique DNA tag comprising a unique sequence of at least 10 nucleotides which is specific to said one of the candidate molecules of the plurality of candidate molecules, such that said one of the candidate molecules of the plurality of candidate molecules are identified by virtue of this unique sequence comprised within the unique DNA tag,
      (4) at least 5% molar of an amphiphilic lipid,
      (5) from 15 to 70% molar of at least one cationic surfactant selected from the group consisting of:
   N-[1-(2,3-dioleyloxy) propyl]-N,N,N-trimethylammonium chloride,
   1,2-dioleyl-3-trimethylamonium-propane,
   N-(2-hydroxyethyl)-N,N-dimethyl-2,3-bis(tetradecyloxy-1-propananium),
   1-[2-(oleoyloxy)ethyl]-2-oleyl-3-(2-hydroxyethyl)imidazolinium, and
   dioctadecylamidoglycylspermine, and
      (6) from 10% to 55% molar of a co-surfactant comprising at least one poly(ethylene oxide) chain comprising between 25 to 500 ethylene oxide units,
      (7) a solubilizing lipid, and
      (8) optionally a fusogenic lipid, wherein the molar percentages of amphiphilic lipid, cationic surfactant and co-surfactant are relative to the total molar amounts of amphiphilic lipid, cationic surfactant, co-surfactant, and optional fusogenic lipid under conditions allowing said cells to be transfected by at least one of said synthetic nanoparticles of the library of synthetic nanoparticle whereby the tracer is integrated within the cells;
   (b) selecting the cells having integrated the tracer and having a phenotype of interest; and
   (c) identifying as a molecule of interest, one of the candidate molecules of the plurality of candidate molecules that has been integrated into the cells selected in (b) by identifying the unique sequence of at least 10 nucleotides of said single unique DNA tag of the plurality of different unique DNA tags.

2. The method for screening method according to claim 1, wherein the tracer is a magnetic tracer and selecting cells that have integrated said magnetic tracer is performed by magnetic cell sorting, or the tracer is a fluorophore and selecting cells that have integrated said fluorophore is performed by flow cytometry.

3. The method for screening method according to claim 1, wherein each synthetic nanoparticle is a particle of less than 1 micron in diameter.

4. The method for screening method according to claim 1, wherein said synthetic nanoparticles further comprise a biological ligand for targeting a cell and/or an organ.

5. The method for screening method according to claim 1, wherein in said synthetic nanoparticle is an oil-in-water nanoemulsion; said fusogenic lipid is 1,2-Dioleoyl-sn-Glycero-3-Phosphoethanolamine; and said amphiphilic lipid is a phospholipid.

6. The method for screening method according to claim 4 wherein, in said synthetic nanoparticle, said co-surfactant is grafted with said biological ligand for targeting a cell and/or an organ.

7. The method for screening according to claim 1, wherein said candidate molecule is a nucleotide sequence which modulates RNA interference mechanisms.

8. The method for screening method according to claim 7, wherein said nucleotide sequence which modulates RNA interference mechanisms is selected from the group consisting of:
 (a) a small interfering RNA (siRNA),
 (b) a locked nucleic acid (LNA),
 (c) a microRNA (miRNA), and
 (d) a long double-stranded RNA (dsRNA).

9. The method for screening method according to claim 1, wherein said single unique DNA tag consists in a sequence of DNA with at least 50 nucleotides or base pairs (bp) selected from the group consisting of, on one strand and in the 5'-3' direction:
 (a) a first sequence of at least 20 nucleotides common to all the single DNA tags of the library,
 (b) a single sequence of at least 10 nucleotides specific to said molecule, and
 (c) a second sequence of at least 20 nucleotides common to all the single DNA tags of the library.

10. The method for screening according to claim 9, wherein said single unique DNA tag comprises double-stranded DNA.

* * * * *